US007811244B2

(12) United States Patent
Soerensen et al.

(10) Patent No.: US 7,811,244 B2
(45) Date of Patent: Oct. 12, 2010

(54) ANATOMICAL CONNECTION

(75) Inventors: Dennis Dam Soerensen, Smyrna, GA (US); Lakshmi Prasad Dasi, Atlanta, GA (US); Keren Pekkan, Athens, GA (US); Diane De Julien de Zelicourt, Atlanta, GA (US); Ajit P. Yoganathan, Tucker, GA (US)

(73) Assignee: Georgia Tech Research Corp., Atlanta, GA (US)

( * ) Notice: Subject to any disclaimer, the term of this patent is extended or adjusted under 35 U.S.C. 154(b) by 717 days.

(21) Appl. No.: 10/593,855

(22) PCT Filed: Mar. 23, 2005

(86) PCT No.: PCT/US2005/009835

§ 371 (c)(1),
(2), (4) Date: Sep. 22, 2006

(87) PCT Pub. No.: WO2005/094521

PCT Pub. Date: Oct. 13, 2005

(65) Prior Publication Data

US 2008/0021368 A1    Jan. 24, 2008

Related U.S. Application Data

(60) Provisional application No. 60/555,515, filed on Mar. 23, 2004.

(51) Int. Cl.
*A61M 1/36*   (2006.01)
*F16K 11/20*  (2006.01)

(52) U.S. Cl. .............................. 604/8; 604/9; 604/264; 137/597

(58) Field of Classification Search ...................... 604/8, 604/9, 264; 128/898
See application file for complete search history.

(56) References Cited

U.S. PATENT DOCUMENTS

| | | | | |
|---|---|---|---|---|
| 5,383,491 | A | * | 1/1995 | Heilman ..................... 137/597 |
| 5,984,955 | A |   | 11/1999 | Wisselink |
| 6,234,203 | B1 |   | 5/2001 | Backlund |
| 2005/0221072 | A1 | * | 10/2005 | Dubrow et al. ............ 428/292.1 |

OTHER PUBLICATIONS

International Search Report for PCT/US2005/009835 dated Mar. 15, 2007.

* cited by examiner

*Primary Examiner*—Leslie R Deak
(74) *Attorney, Agent, or Firm*—Troutman Sanders LLP; Ryan A. Schneider; James Hunt Yancey, Jr.

(57) ABSTRACT

A device for use in the total cavopulmonary connection (TCPC) in order to optimize its hemodynamics. Although the current procedure of choice for single ventricle heart repairs, the TCPC has reduced the post-operative mortality to the level of simpler types of congenital heart disease repairs, Fontan patients are still subjected to serious long-term complications. The TCPC procedure, which restores the vital separation between oxygenated and deoxygenated blood, also leads to an increased workload for the remaining single ventricle, as it is now responsible for pumping the blood through both the systemic and pulmonary circulation. The present device reduces this workload by altering the surgically created design of the TCPC. Improved fluid mechanics and reduced energy dissipation at the connection site translates into less work for the single ventricle and improved transport of deoxygenated blood to the lungs, which may in turn contribute to improved post-operative results and quality of life.

22 Claims, 21 Drawing Sheets

(a) Normal Circulation       (b) Congenital Defects

ANATOMICAL CONNECTION

BENEFIT CLAIMS

This application is a US National Stage of International Application No. PCT/US2005/009835 filed 23 Mar. 2005, which claims the benefit of U.S. Ser. No. 60/555,515, filed 23 Mar. 2004.

GOVERNMENT INTERESTS

This invention was made in part during work supported by the U.S. Government, including grants from the National Institutes of Health (NIH) HL67622-01A1. The government may have certain rights in the invention.

BACKGROUND OF THE INVENTION

1. Field of the Invention

This invention relates generally to a junction device for a plurality of flows, and more specifically to an anatomical or surgically created connection.

2. Description of Related Art

The incidence among other congenital heart defects of children born in the USA with complex congenital heart defects in which there is only one effective pumping chamber is about 20%. Some studies indicate that the overall incidence of congenital heart defects is 1%—and therefore, generally two babies per 1000 births will be born with a single ventricle. If untreated, life expectancy can be short.

Surgical repairs that separate the pulmonary and systemic circuits, placing them in series with the univentricular pump, termed "Fontan Repairs," are palliative, and unfortunately not curative. Operations are routinely staged over many years and survivors often require a lifetime (rather limited) of intensive medical attention. Cardiologists report that their patient populations with this complex cardiovascular physiology (approximately 20%) require a disproportionate share of their time (at least 50%).

The concept of a total right ventricular bypass, first introduced by Fontan and Baudet in 1971, is a palliative procedure aimed at separating the systemic and pulmonary circulations, thus eliminating mixing of oxygenated and deoxygenated blood. The remaining left ventricle drives the blood flow throughout the entire body.

Since its inception, modifications of the Fontan procedure have steadily improved surgical outcomes, reducing the post-operative mortality to the level of more simple types of congenital heart disease repairs. However, the marked improvement in surgical outcome is balanced by the numerous and serious long-term complications encountered by the Fontan patients, such as ventricular dysfunction, thromboembolism, arrhytmias and protein loss enteropathy.

As a general background, in the cardiovascular system, blood is a major means of transportation for the nutrients and wastes that travel to and from the body's tissues. It is pumped through the entire body by the heart, and then perfuses each single tissue through a complex network of arteries, capillaries and veins. The cardiovascular circulation can be subdivided into two primary circuits: the pulmonary and systemic circulations. The pulmonary circuit describes the path going from the heart to the lungs and back, and the systemic circulation transports the blood between the heart and the remainder of the body.

The normal heart has four chambers: the left and right atria and the left and right ventricles. In a normal physiology the septum separates the left and right sides of the heart creating two distinct pumps that function in parallel. The left side of the heart drives the blood through the systemic circuit, while the right side drives the blood through the pulmonary circuit.

This four-chambered structure of the heart is essential to its function. The ventricles provide the pumping force, while the atria provide the buffer volume needed to receive the continuous blood flow returning from the body or the lungs. In addition to these four chambers, four valves control the inlet and outlet of both ventricles to prevent blood-flow reversal and ensure the efficiency of the ventricular contraction. When the left ventricle contracts during systole, the increase in ventricular pressure closes the bileaflet mitral valve and forces the trileaflet aortic valve open. Consequently, most of the blood that was present in the left ventricle before systolic contraction must flow from the left ventricle through the open aortic valve into the aorta then to the rest of the body.

Meanwhile, the blood returning from the lungs through the pulmonary veins is stored in the left atrium. As pressure builds up in the left atrium and in the aorta and decreases in the left ventricle during diastole, the mitral valve reopens and the aortic valve closes. Blood then flows from the left atrium through the mitral valve into the left ventricle.

Similarly, the systemic blood coming back from the body flows through the inferior vena cava (IVC) and superior vena cava (SVC) into the right atrium. It then passes through the tricuspid valve into the right ventricle from where it is discharged through the trileaflet pulmonary valve into the pulmonary circulation for gas exchange.

Congenital heart defects (CHDs) describe all abnormalities of the heart or of the great arteries (pulmonary arteries and aorta) that are present at birth. They are the leading cause of infant mortality in the western world accounting for about 20% of all infant death. CHDs alone account for one-third of all birth defects affecting one in every 100 infants in the United States. They are the number one cause of birth defect related deaths during the first year of life, and the mortality of these children may be as high as 50% depending on the condition.

CHDs arise from faulty embryogenesis between the third and eighth week of gestation, when major cardiovascular structures develop—going from a simple straight tube to a complex four-chambered heart with separate pulmonary and systemic circuits. Over 35 different forms of CHDs have been reported, and although the exact cause of CHDs is still unknown in most cases, multifactorial genetic and environmental parameters, including chromosomal defects, viruses, chemicals and radiation are suspected.

Among all CHDs, particularly challenging are the defects (or combination of defects) observed in about 20% of the CHD cases that effectively lead to a single ventricle (SV) anatomy. This physiology results in communication between the systemic and pulmonary circulation, thereby eliminating the two-pump system and allowing for the mixing of oxygenated and deoxygenated blood. It is well understood that venous blood mixing should be avoided, and corrected if possible.

FIG. 1 is a schematic showing differences between normal, single ventricle, and Fontan physiology. In a normal physiology, the vena cavae contains deoxygenated blood coming from the systemic circulation and the pulmonary arteries carries the deoxygenated blood from the right ventricle to the lungs for the blood to become oxygenated.

The single ventricle physiology pumps high pressure blood to both the systemic and the pulmonary circulation. The high pressure in the pulmonary circulation and the mixing of oxygenated and deoxygenated blood causes many of problems, which is why the Fontan procedure is performed. The current Fontan surgical procedure of choice for patients with single ventricle physiology is the total cavopulmonary connection (TCPC).

The most prevalent CHDs leading to a SV anatomy include multiple ventricular and/or atrial septal defects, tricuspid atresia, hypoplastic left or right heart syndrome, transposition of the great arteries, and a double inlet ventricle.

Without surgical intervention, survival of patients with blocked right or left heart pathways as a result of a transposition of the great arteries, a tricuspid atresia or an acute hypoplastic heart syndrome once depended on the presence of coexisting defects such as a septal defect or a patent ductus arteriosus. In the middle of the $20^{th}$ century, surgical shunt procedures were developed as a palliative procedure for cyanotic CHD. The purpose was to connect the pulmonary arteries (PAs) with the systemic arteries or with the SVC so as to try and augment the pulmonary blood flow.

These shunts enabled short-term survival. However, ventricular dysfunction, pulmonary vascular disease, and chronic cyanosis prohibited a normal existence and drastically shortened patient life expectancies with only few patients surviving beyond adolescence.

The advent of the Fontan operation in 1971 brought about a revolution in the management of single ventricle heart defects. In a Fontan type circulation, the left ventricle pumps blood into the aorta and arteries. This blood flows at first rapidly into the different organs. The very same force pushes the blood across capillaries, and through the veins. But by its very nature, this flow depends on many factors. For instance, if the blood vessels in the lung are thick walled and narrow before surgery, they will offer very high resistance to passive blood flow. In such a state, the Fontan operation cannot be performed, or will have a high risk of failure, since the extra energy needed to maintain lung blood flow is not available.

Even normally some amount of resistance will exist across the lung blood vessels. After a Fontan operation, the pressure in the veins will therefore be higher than normal, in order to overcome this resistance and maintain lung blood flow. The elevated pressure in the veins has a few ill effects, including that there may be swelling of the entire body due to fluid from the blood leaking out of the vein walls, there may be facial puffiness, fluid accumulation in the abdomen (ascites) or chest (pleural effusion), and sometimes even absorption of nutrients from the intestines is affected.

Indeed, the heart may eventually fail. The age at which the heart fails and the patient requires a heart transplant depend on many different factors, but a main reason appears to be the excessive workload placed on the single ventricle. The major causes of death are: heart failure, arrhythmia, protein losing enteropathy, and embolisms.

The principle of a complete right heart bypass, where the systemic veins were directly connected to the pulmonary arteries without going through the single ventricle, achieved a number of salutary transformations to the SV anatomy. It re-separated the systemic and pulmonary circuits and eliminated venous blood mixing, which in turn ostensibly improved arterial oxygen saturation and patient color.

The original Fontan procedure included the construction of two independent VC-to-PA tracks, the IVC-to-LPA and SVC-to-RPA, with the anastomosis of the right atrium directly onto the PAs and a valve placed in the IVC.

However, it soon became clear that placing a valve in the caval conduits, rather than being advantageous, resulted in obstruction of the low-pressure VC-to-PA circulation. Furthermore, the separation of the IVC-to-LPA and SVC-to-RPA tracks, that had been designed to ensure an even perfusion of the right and left lungs, did not allow for any adaptation of the LPA/RPA blood flow ratio, leading to serious complications when one of the pulmonary tracks became obstructed. Additionally, such a cardiovascular configuration excluded all hepatic blood flow from the RPA, which was demonstrated to be strongly correlated with pulmonary venous malformations.

Shortly after the first successful right ventricular heart bypass operation for tricuspid atresia, a modified Fontan procedure was demonstrated wherein the entire venous return could be diverted to the pulmonary circulation through a single valveless atrio-pulmonary (AP) connection. This procedure had the combined advantages of providing the pulsatile action of the atrium, redistributing the hepatic fluid to both lungs and splitting the pulmonary blood flow depending upon the needs and resistance of either lung.

The valveless AP-connection was the first in a series of modifications of the original Fontan procedure. Although this procedure was quickly endorsed and has had widespread use in many centers, the long-term follow-up of patients with an AP-connection indicated that they were prone to late complications. Patients developed supraventricular arrhytmias, right atrial thrombus, exercise intolerance and other symptoms of low cardiac output. These complications were usually related to a markedly dilated right atrium appendage, which was suspected to be due to the increased pressure load imposed on the atrium. This atrial dilatation was in turn associated with stagnant flows along the dilated right side of the atrium and turbulent flows elsewhere in the connection, resulting in significant fluid energy dissipation.

The high incidence of right-atrium related complications led many to question the role of the pulsating right atrium and its actual contribution to the Fontan circulation. There was in vitro and in vivo evidence that the interposition of a passive chamber with impaired systolic function between the VCs and PAs was a major cause of flow inefficiency, and the total cavopulmonary connection was proposed as a logical alternative to the Fontan procedure.

The TCPC has been described as the anastomosis of the SVC directly onto the RPA followed by the creation of a tunnel through the right atrium connecting the IVC to the inferior aspect of the RPA. This geometry has been demonstrated to lead to more streamlined flow patterns with less turbulence and fluid energy loss when compared to the AP-connection. These findings were confirmed both by in vitro and computational fluid dynamic studies. Retrospective clinical studies also investigated early and late mortality rates. Findings show that the TCPC is accompanied by a lower mortality rate, improved outcomes and a more favorable course during the postoperative period.

Staging the operations has markedly improved surgical outcomes, and allowed the Fontan surgery to be applied to a larger range of SV-patients. It is now an integral part of the methodology for SV heart repairs. Usually, there are three different stages involved in the completed "Norwood procedure" leading to the resultant Fontan—each stage with inherent morbidity and associated mortality.

The first stage is commonly performed immediately after birth or within the first two weeks of life and is referred to as the first stage Norwood or Norwood I procedure. It involves creation of a systemic to pulmonary arterial connection, arch reconstruction and coarctation repair with anastamosis of the native aorta to the pulmonary arterial trunk (also called the Damus-Stancil-Kaye procedure) and an atrial septectomy.

A more recent modification, the "Sano" procedure, involves placement of a right ventricle to pulmonary arterial connection and elimination of the systemic to pulmonary arterial shunt.

The second stage bi-directional "Glenn" procedure (Norwood II), performed at approximately three to four months of age, involves anastamosis of the superior vena cavae to the pulmonary arteries and removal of the systemic to pulmonary shunt or the RV to PA shunt and has the lowest reported risk.

The last stage (Norwood III), or Fontan procedure is creation of a connection of the inferior vena cavae to the pulmonary arteries via an intra-atrial or extra-cardiac connection. This results in the total cavopulmonary connection.

Although most surgeons agree on the staged TCPC as being the current procedure of choice for Fontan repairs, controversies exist about the selection of the connection type, the type of material to use, the need for fenestration, and the timing of the operations.

The choice of connection type seems to be dictated by surgeon preference, each type with pros and cons. When compared to intra-atrial tunnels, extra-cardiac conduits provide numerous advantages including smoother geometries, fewer atrial suture lines thus minimizing sinus-node damage, and less or no time on the heart- lung machine. On the other hand they provide no growth potential and may lead to conduit stenosis and thromboembolism. Although long-term follow-ups are not yet available, early- and mid-term results for extra-cardiac conduits are favorable, especially combined with a fenestration in the inferior conduit.

Including a fenestration has been demonstrated to lower the systemic venous pressures as well as to improve ventricular filling, consequently leading to improved cardiac output and overall oxygen delivery. While some institutions advocate systematic fenestration, others argue that it should be used more selectively, balancing the potential benefits against the risks and costs of the additional intervention needed to close the fenestration.

Similarly, the material of choice varies from institution to institution and patient to patient. Intra-atrial tunnels have been built out of polytetetrafluoroethylene (PTFE) patches, pericardial patches and autologous pericardial patches. Extra-cardiac conduits have been constructed using PTFE, Dacron, and autologous pericardium flaps. Mid-term results have been favorable for all synthetic materials and only short-term follow-up data (30 months) is available for autologous conduits.

Finally, as to the timing of the operation, the mean age at TCPC completion and mean interval since previous palliation have significantly decreased over the past decade. While some see this as a beneficial trend that has reduced most of the major complications, others recommend caution pointing out that suture lines significantly limit vessel growth and that vessel size is a major factor for hemodynamic efficiency.

Thus, it can be seen that although various cardiac repair options are known, there is still much room for improvement. Indeed, this should not take away from the success of the Fontan procedure. It is simply that connecting the vena cavae directly to the lungs, bypassing the heart, is a difficult task for the single ventricle due to chronic work and volume overload.

In FIG. 2(a), the normal operating circulation with the two (left and right ventricles) pumping action of the heart is illustrated. The resistance and pressure values shown are representative average values for a healthy adult person measured clinically by catheterization. FIG. 2(a) is a schematic of normal circulation—lumped representation of pulmonary and systemic beds. FIG. 2(b) illustrates various congenital heart defects. The systemic vascular resistance ($R_{sys}$) is approximately 17.5 mmHg/L/min on average, and the pulmonary vascular resistance ($R_{pul}$) is approximately 1.8 mmHg/L/min on average.

As used in FIG. 2, pu is a pulmonary bed (lungs); sys is a systemic bed (upper and lower body combined); PDA is the patent ductus arteriosus; (x) illustrates the flow restriction at aorta; arrows represent the blood flow directions and cardiac shunts; $R_{tri}$ is the tricuspid valve resistance; $R_{pulv}$ is the pulmonary valve resistance; $R_{mi}$ is the mitral valve resistance; and, $R_{ao}$ is the aortic valve resistance.

Constant representative resistance values are used, although it will be understood by those of skill in the art that vascular resistances are regulated to some extent by the body in response to blood pressure, the changing oxygen saturation during exercise, and vary slightly with flow pulsatility. Further, newborn children have higher pulmonary resistance values.

An average blood flow rate (i.e. cardiac output) for normal adults at rest is 5 L/min. For children with the TCPC, the total cardiac output is closer to 3 L/min. Cardiac output can be as high as 20 L/min during exercise conditions for normal adults and in some athletes it goes even higher.

The resistances of the right and left hearts are mainly due to the resistances of the heart valves which are small (~1.5 mmHg/L/min) compared to the vascular resistances unless there is valve stenosis or other problems.

As previously explained, one-fifth of congenital heart defects require a series of complex palliative surgeries which result in a single operating ventricle with the pulmonary and systemic beds arranged in series, as shown in FIG. 3. This configuration results in higher pressures in the systemic bed with severe clinical consequences. FIG. 3 illustrates single ventricle circulation after final stage Fontan surgery. $R_{TCPC}$ is the equivalent TCPC resistance calculated from in vitro experiments for an intra-atrial patient specific anatomy.

There are two versions of the TCPC namely, extra-cardiac and intra-atrial. Yet, current extra-cardiac and intra-atrial TCPC yields high energy losses in the blood flow because of the mixing of the blood. FIGS. 4 and 5 shows models of the TCPC with a transparent blood analog containing particles flowing through the connection. FIG. 4 illustrates an in vitro glass model of a "zero" offset TCPC. FIG. 5 illustrates an in vitro model of a one diameter offset and flared model of a Cavopulmonary Connection.

The two inlets (SVC and IVC) and the two outlets (RPA and LPA) are shown in different configurations. As can be seen from the two figures, there is a region of the connection where there is a high level of venous flow mixing and disturbance. Such a region exists as the inlets either present inlet flows at 180 degrees from one another, forcing the flows to collide head on, before separating toward the two outlets, or the inlets do not provide such a direct path of collision, but even with offset of some amount, the inlet flows nonetheless collide with each other or with a wall sufficiently to present outlet flows with marked energy loss.

The region of mixing in present connection designs negates the beneficial momentum present in the two inlet flows that exists before the blood in the IVC and SVC enter the connection site, wherein the momentum loses due to swirling, turbulence, and other collision characteristics, limits the outlet flows to the lungs.

In this mixing region of the connection, there is a lot of swirling of the flows, when the blood analogue from the inlets mix, which causes substantial energy loss, causing the outlet flow to lose momentum towards the lungs via the two outlets. This is known disadvantage with the current configurations used for Fontan procedures.

RPA/LPA flow splits of 30/70, 40/60, and 50/50 in the models of FIGS. 4 and 5 have shown that when an equal flow goes to both the RPA and the LPA, there is the least amount of energy loss in the flow. Furthermore, the energy loss in the flow increases the more the vessel diameters in the connection are different. Thus, energy loss in the flow is minimized with equal flow in the vessels.

The current Fontan connection typically resembles a mix of FIGS. 6 and 7, thus giving rise to substantial energy losses due to disadvantageous inlet flow collision. FIG. 6 illustrates a one diameter offset planar TCPC model. SVC and IVC diameters are more representative of the in vivo dimensions. FIG. 7 illustrates a TCPC model incorporating non-planar arrangement of pulmonary arteries, wherein FIG. 7(a) shows a front view, and FIG. 7(b) a top view of the same connection. The FIG. 7 model also incorporates a one diameter caval offset; however, all vessels are assumed to be the same size.

While, experimentally, the model of FIG. 5 shows good results compared to the others, nutritious blood coming from the hepatic veins goes primarily to one lung, increasing the size and functionality of this lung compared to the other lung, and this is not optimal.

It is evident that current anatomical connections provide non-optimal energy loss in the flow at regions of the connection where there is a high level of venous flow mixing and disturbance. There is thus a need for an anatomical connection providing optimized flow control, equal distribution of hepatic blood to both lungs, and minimized energy loss, that in effect minimizes or elimates inlet flow collision. It is the provision of such a connection that the present invention is primarily directed.

BRIEF SUMMARY OF THE INVENTION

Among the multiple variables that determine the outcome and the quality of life of patients with ventricular bypass, one that allows for some degree of control is the design of the bypass connection. The present invention is a connection scheme that was developed with a critical review of the hemodynamics/fluid dynamics at the bypass connection site, in order to optimize the connection design to minimize momentum loss in the connection as between the inlet flows, and the outlet flows.

In the total cavopulmonary connection, the inferior venae cavae (IVC) and the superior venae cavae (SVC) are anastamosed directly onto the pulmonary arteries (PAs), forming for the most part a "plus"/"+"-shaped connection, having two inlets approximately 180 degrees from one another, and two outlets, also at approximately 180 degrees. See FIG. 4, for example.

It will be understood that at the intersection of the + design, the two inlet flows will collide head on, diffusing much of the momentum of the two inlet flows prior to collision, before the site of mixing splits into the two outlets.

It would be beneficial if a TCPC connection could be designed to limit the momentum loss from flow inlet to flow outlet. If the region of head-on mixing of the inlet paths of present TCPC connections were limited in size, or indeed eliminated, then a far greater amount of the full momentum of the two inlet flows could be directed to the lungs with little energy loss from the IVC and SVC flows.

The present invention is a connection geometry that provides superior streamlined flow patterns with less disturbance and fluid energy loss when compared to present connections. In other embodiments, the device can be described as limiting flow turbulence, unsteadiness, instability, oscillations, or unwanted secondary flows.

Briefly described, in preferred form, the present invention is an improvement in TCPC hemodynamics and geometry, providing a device that in essence eliminates any regions of inlet flow mixing other than parallel flow stream mixing. The preferred connection comprises a two-inlet, two-outlet connection for optimized flow control and reduced fluid energy losses.

The IVC and SVC flow paths are bifurcated, and one each of the bifurcated flow paths of the IVC and SVC then rejoined with the corresponding path to provide a parallel flow path configuration to the outlets. The design characteristics of this connection used with the two-inlet blood vessels (IVC and SVC) and two-outlet blood vessels (RPA and LPA) minimizes disturbance, swirling, stagnation, and stagnant flow, resulting in reduced energy loss. Reduction in energy losses is desired for several reasons, namely: (1) reduced pressure build-up in the blood vessels especially in the abdominal region, (2) reduced workload on the left ventricle, (3) increased ability of the heart to support activities such as running or other exercise. Further, a reduction in the risk of thrombus and emboli formation can be had with the present invention as it minimizes the amount of flow recirculation and stasis.

The disturbance, swirling, stagnation, stagnant flow, and energy loss is reduced in the present invention as each of the two inlets bifurcate in two paths, a left path and a right path. The left and right paths gently guide the inlet flows through, for example, 90 degrees. The connection has a top inlet, a bottom inlet, a left outlet, and a right outlet. The top inlet is split into a left path and a right path, as is the bottom inlet. Inlet blood flow from the top inlet that is diverted to the top left path is combined with the inlet blood flow from the bottom inlet that is diverted to the bottom left path. The two left path flows of the original IVC and SVC flows mix with vectors of the same bearing, thus limiting momentum loss and mixing.

Similarly, inlet blood flow from the top inlet that is diverted to the top right path is combined with the inlet blood flow from the bottom inlet that is diverted to the bottom right path. Thus, the two right path flows of the original IVC and SVC flows also mix, but with common vectors of travel, thus limiting momentum loss.

The inlet flows in the current design therefore do not meet at a site of collision or high disturbance like in present connections, but merge together in at least approximately parallel flows, providing less flow separation, and a mixing of the IVC and SVC blood flow preferably only at the two outlets, not at some central region of mixing in the connection.

The present connection can furthermore be used to control inlet, outlet, and path flows by decreasing or increasing the vessel diameters. The connection may be fashioned from existing blood vessels, graft materials, or a combination of both.

The preferred environment for the present invention are in blood vessel connections where there are two inlets and two outlets, and optimal flow is desired, as well as some control of pressures and flows by changing vessel diameters. The present invention is primarily intended for patients with a single ventricle who undergoes the Fontan surgery. While the connection can be located in the body at the site of the heart, it is possible to have in vitro, in vivo and ex vivo connection embodiments utilizing the present invention.

The present invention provides advantages over the conventional connection geometries as it reduces swirling, disturbance, stagnant flow, and by enabling the changing of diameters of the vessels, the flow and pressure can be fully controlled in all four vessels.

These and other objects, features and advantages of the present invention will become more apparent upon reading the following specification in conjunction with the accompanying drawing figures.

BRIEF DESCRIPTION OF THE FIGURES

FIG. 7 illustrates a prior art TCPC model incorporating anatomically realistic non-planar arrangement of pulmonary arteries, wherein

FIG. 19 illustrates the environment of use for the center piece embodiment of the present invention of FIG. 18.

DETAILED DESCRIPTION OF PREFERRED EMBODIMENTS

Figure 1:
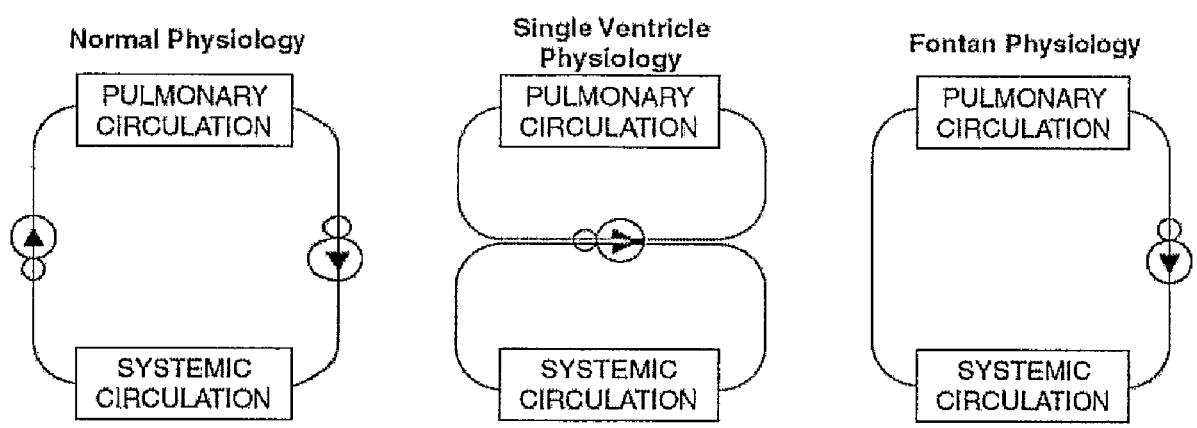
FIG. 1 is a schematic showing differences between normal, single ventricle, and Fontan physiology.
Figure 2:
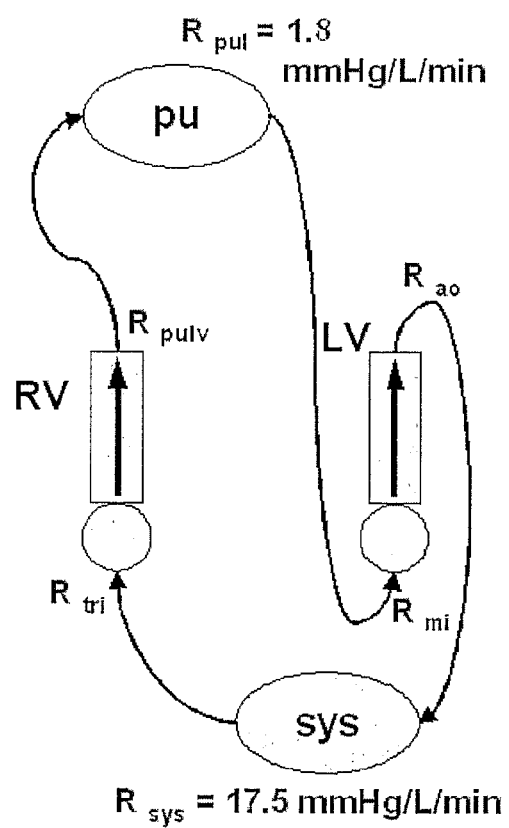
FIG. 2(a) is a schematic of normal circulation.
FIG. 2(b) illustrates various congenital heart defects.
Figure 2:
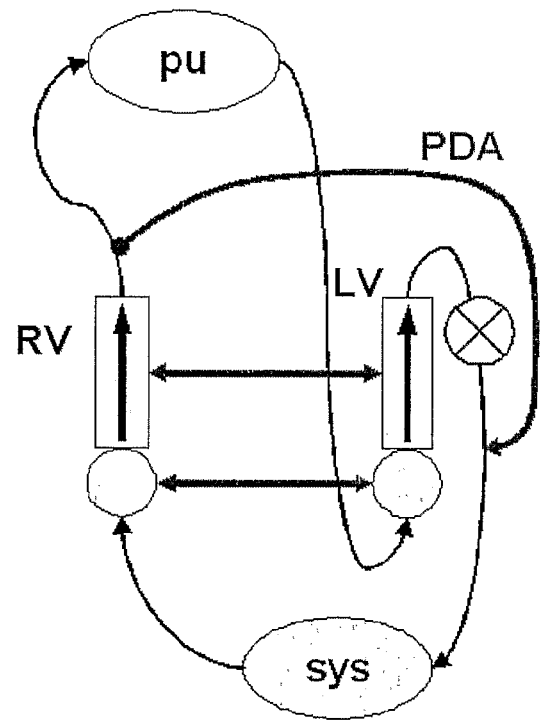

Referring now in detail to the drawing figures, wherein like reference numerals represent like parts throughout the several views, the present invention preferably is a method of limiting flow turbulence in an energy efficient manner, and a device for same. A preferred method of present invention includes the steps of providing a flow merging device, splitting a first inlet flow at the flow merging device into a first branch and a second branch, splitting a second inlet flow at the flow merging device into a first branch and a second branch, and merging the first branches of the first and second inlet flows together, wherein the flows in each of the first branches are substantially parallel at the site of merging.

The present invention is a flow merging device, designed to take what are generally two inlet flows traveling at different directions (commonly at approximately 180 degrees from one another), and providing a flow combination scheme that combines the inlet flows not head on, but when they are in the same direction of travel. That is, provide outlet flow paths that do not require the inlet flows to mix at anything less than common vectors of travel.

In one preferred embodiment of the present invention, the method and device for use in bypassing the right side of the heart, and redirecting the venous blood flow from the systemic to the pulmonary circulation in an energy efficient manner, wherein a multiple-inlet, multiple-outlet connection is used to bifurcate each of the incoming venous flows, and appropriately redistribute the split flows to each lung, wherein the act of splitting the inlet flows is performed in an energy efficient manner, reducing flow resistance, swirl, and helicity, as well as the amount of recirculation and flow stasis.

It will be understood that the present invention can either foster proper vessel orientation, or can itself provide the pathways for blood flow. That is, the invention can be a flow merging device wherein vessels are attached to inlet(s) and outlet(s), and the flow is within the device, or the present invention can be of a center piece construction, such that the center piece fosters blood flow around itself (as opposed to within itself).

A preferred method of the present invention is a method of combining the IVC and SVC flows at zero offset by utilizing a device that diverts the incoming IVC and SVC flow streams before they would normally intersect at a common point of collision, and divert them into as close to parallel flows as practical before allowing them to smoothly combine, to then travel to the lungs.

The invention preferably comprises a first connection inlet for inferior vena cava, and a second connection inlet for the superior vena cava. Each of the first and the second connection inlets are themselves bifurcated, such that the desired amount of flow of each of the inferior and the superior vena cava are directed to outlets of the device.

A first connection outlet provides a blood flow path for the merging of a desired amount of the inferior vena cava flow, and a desired amount of the superior vena cava flow, wherein the margining of these two flows is parallel. A second connection outlet provides a blood flow path for the merging of the second amount of the inferior vena cava flow, and the second amount of the superior vena cava flow.

The device thus alters the flow combination of the inferior vena cava and the superior vena cava from essentially 180 degrees, to zero degrees, such that instead of the flows colliding head on before traveling to the lungs, they merge smoothly into each other in parallel flows.

The present invention is preferably a two-inlet, two-outlet tubular member, wherein vessels terminate at the inlet and outlet ports of the connection, the member so designed to avoid direct collision of the caval flows. The present invention facilitates minimal flow energy loss and provides preferably equal amounts of nutrient filled hepatic blood to both lungs.

The invention can be tubular, and can take other shapes, such as elliptic, squared, hexagonal, octagonal, and triangular.

The present connection need not necessarily be planar, as inlets and/or outlets can each be in different planes. The angle between inlets, and the angle between outlets, need not be 180 degrees, although that is shown in many of the Figs. Similarly, the angle between an inlet and outlet can be different than 90 degrees.

While the present device can be used in numerous environments, diameters for anatomically purposes are rarely equal. Preferably, the diameters of the inlets/outlets of the connection should match the vessels attached thereto. Diameter mismatch between the device and the vessels can cause increases in power loss.

The device is preferably an anatomical connection used for the heart, but it will be understood that the connection can be used in other parts of the body with various fluid flows. For example, the connection can be used where blood needs to be diverted either in the venous or arterial circulation.

The present device can be used in conjunction with a pump. With a two inlet device, for example, by having a pump before one inlet to boost the flow, the flow from the other inlet will automatically be increased too, due to the suction effect at the outlet connections sites.

The device can include fins/obstructions in the pathways that can be used to reduce secondary flow, swirl, and helicity.

While the connection device can be used in both humans, and other animals, it can be used in non-anatomical flow environments, like engines, combustion, pipe lines, and plumbing. The connection device may also be used in non-fluid or flow connections, for example, for electric currents, wave guides and optical connections. In such high frequency communication carrier embodiments (optical and electric), the invention can be, for example, be an optical booster, optical splitters, and wave guide splitter/connection. As such, the present device can be constructed of, among others, metals, glass, plastics, transparent materials in general, and insulation materials (thermal, electromagnetic, and electric).

The present device can be used in optical connections/ applications, for example, splitting optical fibers from one inlet to two outlets, where the second inlet is used to boost the power of the signal. Presently, an optical fiber signal can be boosted by having a y-shaped connection, with two inlets: one with a weak signal, another with a power boost input, and this amplifies the weak signal coming out of the one outlet. This is, for example, used to boost signals in transoceanic optical fibers.

Figure 17:
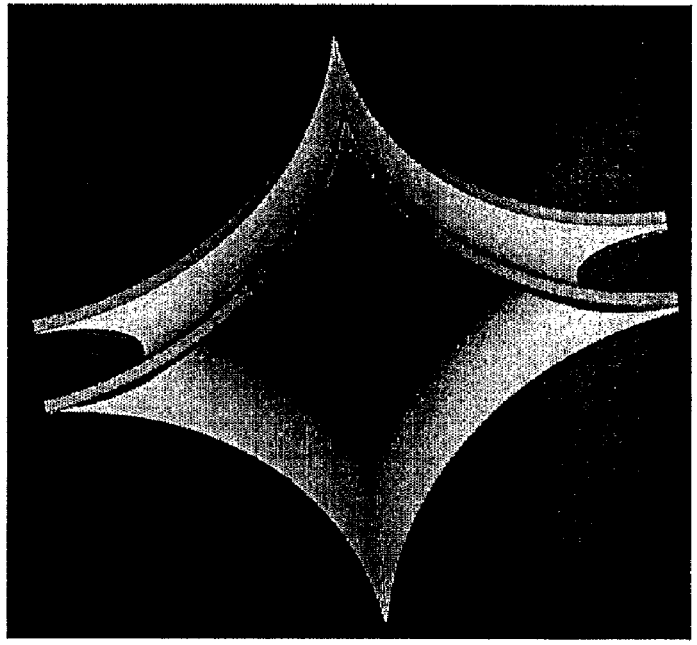
Figure 18:
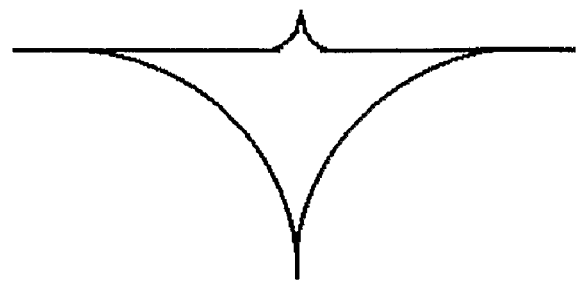
Figure 19:
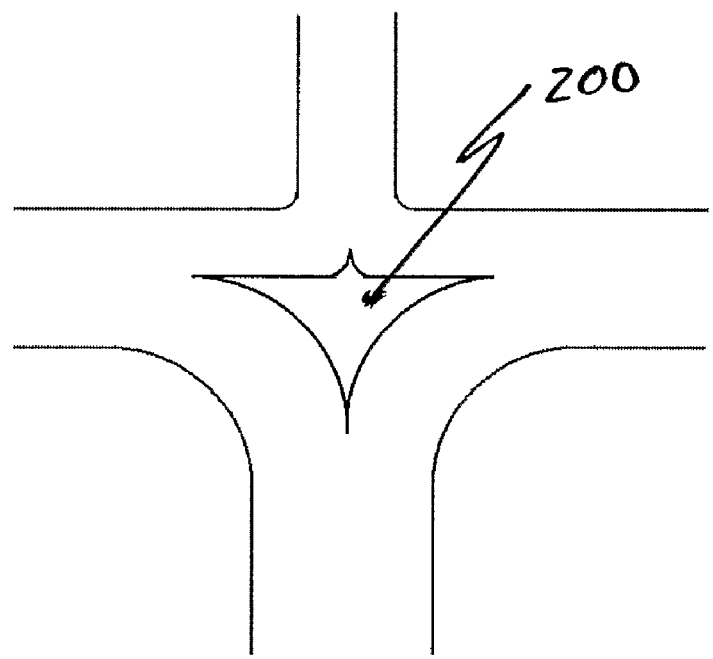
Figure 20:
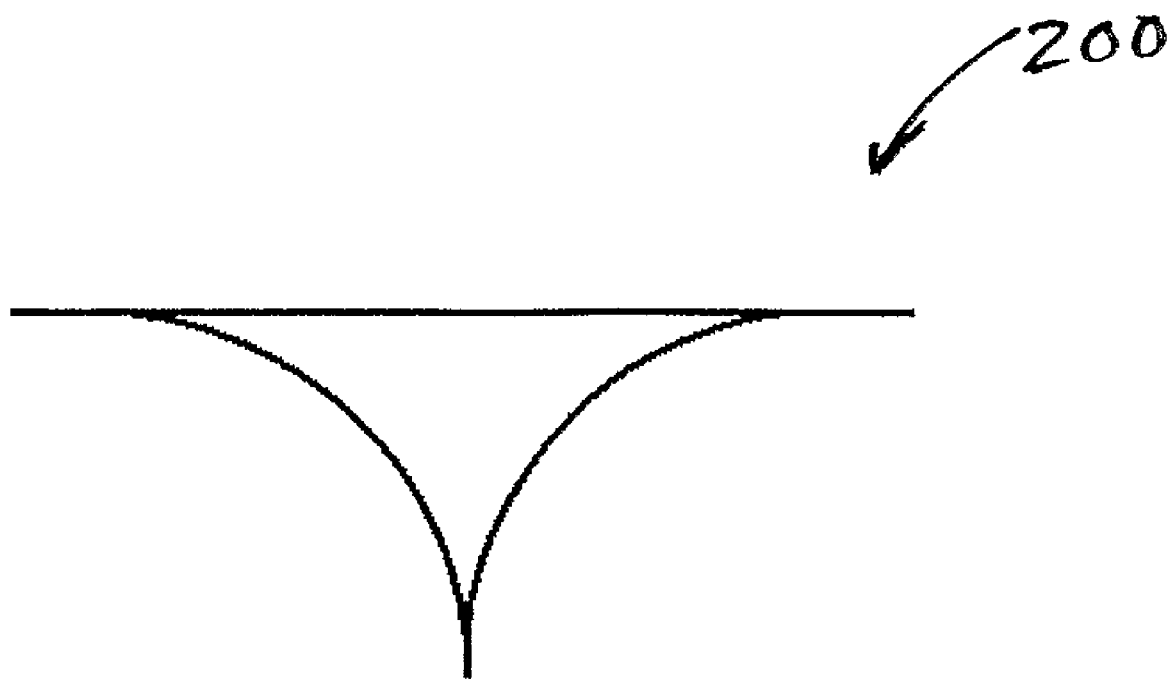

FIGS. 8-20 show various preferred embodiments of the present invention 100. The embodiments of FIGS. 8-15 illustrate tubular-like connection members, wherein the vessels attach directly to the inlets/outlets of the device. The present invention 100 of FIGS. 8-15 is a self-contained, tubular structure, wherein vessels terminate at the inlets/outlets, and blood flows within the device. FIGS. 16-20 illustrate another general embodiment of the present invention, wherein the device is a center piece 200, being a flow merging device that provides an internal infrastructure or framework to bifurcate the flows of the IVC/SVC. The device 200 of FIGS. 16-20 comprises a connection system that allows blood flow to continue through connected vessels, and simply properly orients the vessels and flow therein. FIG. 19 illustrates an example of environment of use for the center piece embodiment 200 of the present invention of FIG. 18. The device of FIG. 20 is for use as a center piece graft in the case where there are two SVCs, for example, and the devices of FIGS. 18 and 19 do not work well.

Figure 8:
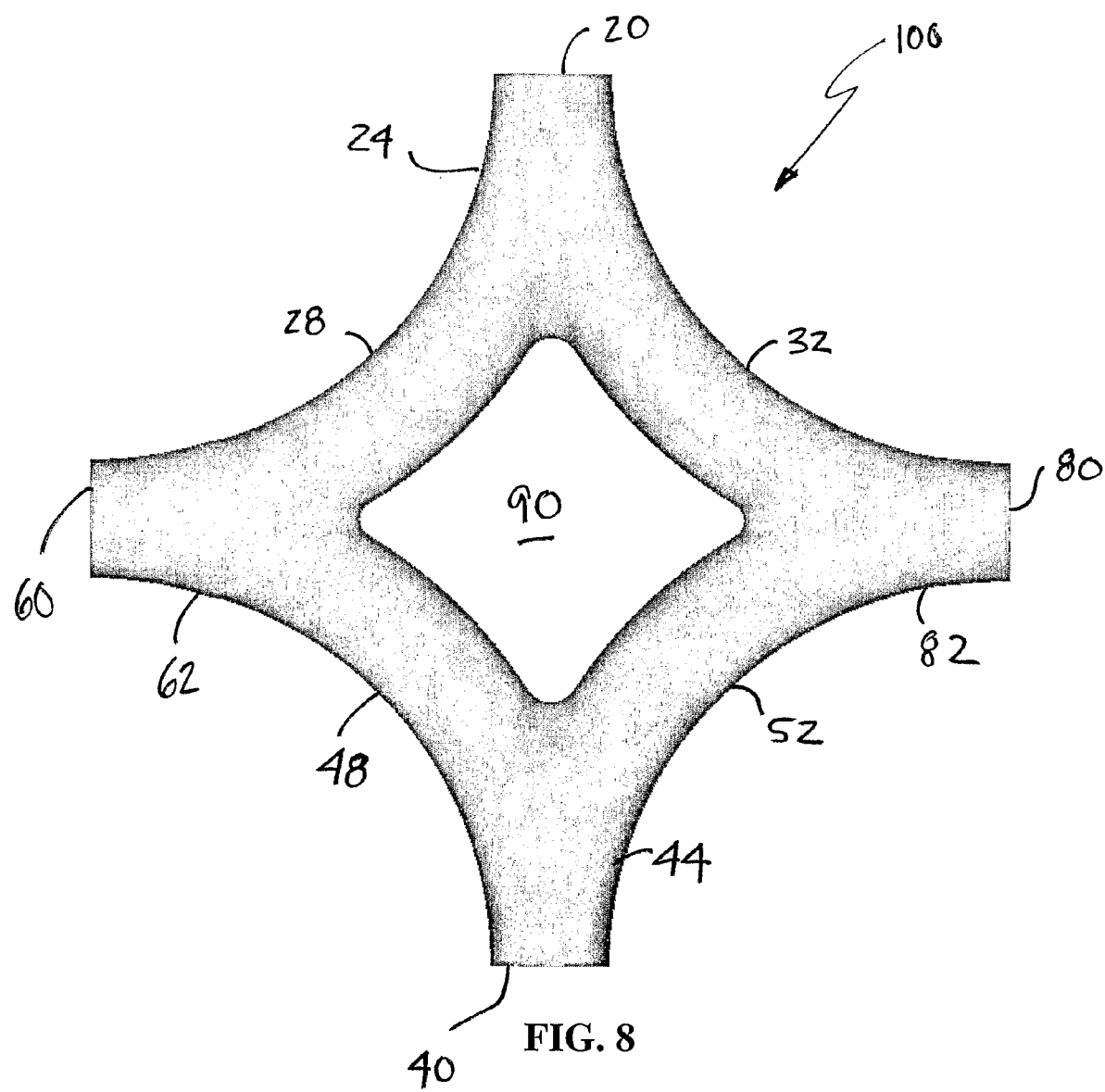
FIG. 8 is a preferred embodiment of the present invention.

The invention 100 of FIG. 8 preferably comprises a first connection inlet 20, a second connection inlet 40, a first connection outlet 60 and a second connection outlet 80. For ease of discussion only, the first connection inlet 20 could be for the SVC, the second connection inlet 40 for the IVC, the first connection outlet 60 the RPA path, and the second connection outlet 80 the LPA path.

Although the inlets 20, 40 are shown at 180 degrees from each other, and the outlets 60, 80 too shown at 180 degrees from each other, they need not be so orientated, nor in the same planes. The goal of the present invention is mainly to eliminate the region 90, which in prior art connections with the region where the inlet flows collide with one another. As shown in FIG. 8, the region 90 of the present invention is indeed not a part of the device 100, but an area that is designed around by the bifurcation of the inlet flow paths before reaching such a region of intersection.

The first connection inlet 20 comprises a first connection inlet chamber 24 prior to the inlet 20 splitting in a first outlet path 28 and a second outlet path 32. The second connection inlet 40 comprises a second connection inlet chamber 44 prior to the inlet 40 splitting in a first outlet path 48 and a second outlet path 52. Chambers 24, 44 are simply lengths of the inlets of the device 100 wherein the IVC/SVC flow has not yet been split.

The first connection inlet 20 and the second connection inlet 40 preferably are in the same plane, and at 180 degrees from one another. Inlets 20, 40 further preferably have the same diameter as the vessels they are each attached to (which, in the case of IVC/SVC connections, are not the same), and split the flow between their respective outlet paths 28, 32 and 48, 52 evenly.

First outlet paths 28, 48 then merge to enable the combined flow to commonly exit first connection outlet 60. First connection outlet 60 has a first outlet chamber 62 into which the outlet paths 28, 48 lead, prior to the flow exiting the outlet 60.

Second outlet paths 32, 52 merge to enable flow to exit second connection outlet 80. Second connection outlet 80 has a second outlet chamber 82 into which the outlet paths 32, 52 lead, prior to the flow exiting the outlet 80.

The first connection outlet 60 and the second connection outlet 80 preferably are in the same plane, and at 180 degrees from one another. Outlets 60, 80 further preferably have the same diameter.

Thus, blood flow enters the connection 100 in from opposite vessels, and exits in two other opposite vessels. The invention of FIG. 8 is symmetrical about the x, y, and z planes, although the connection need not be so designed. Further, the paths 28, 32, 48, 52 are shown with uniform diameter along their length, and with each other, although the diameter of the paths 28, 32, 48, 52 need not be so uniform, nor do the diameters of inlets and outlets 20, 40, 60, and 80.

Figure 10:
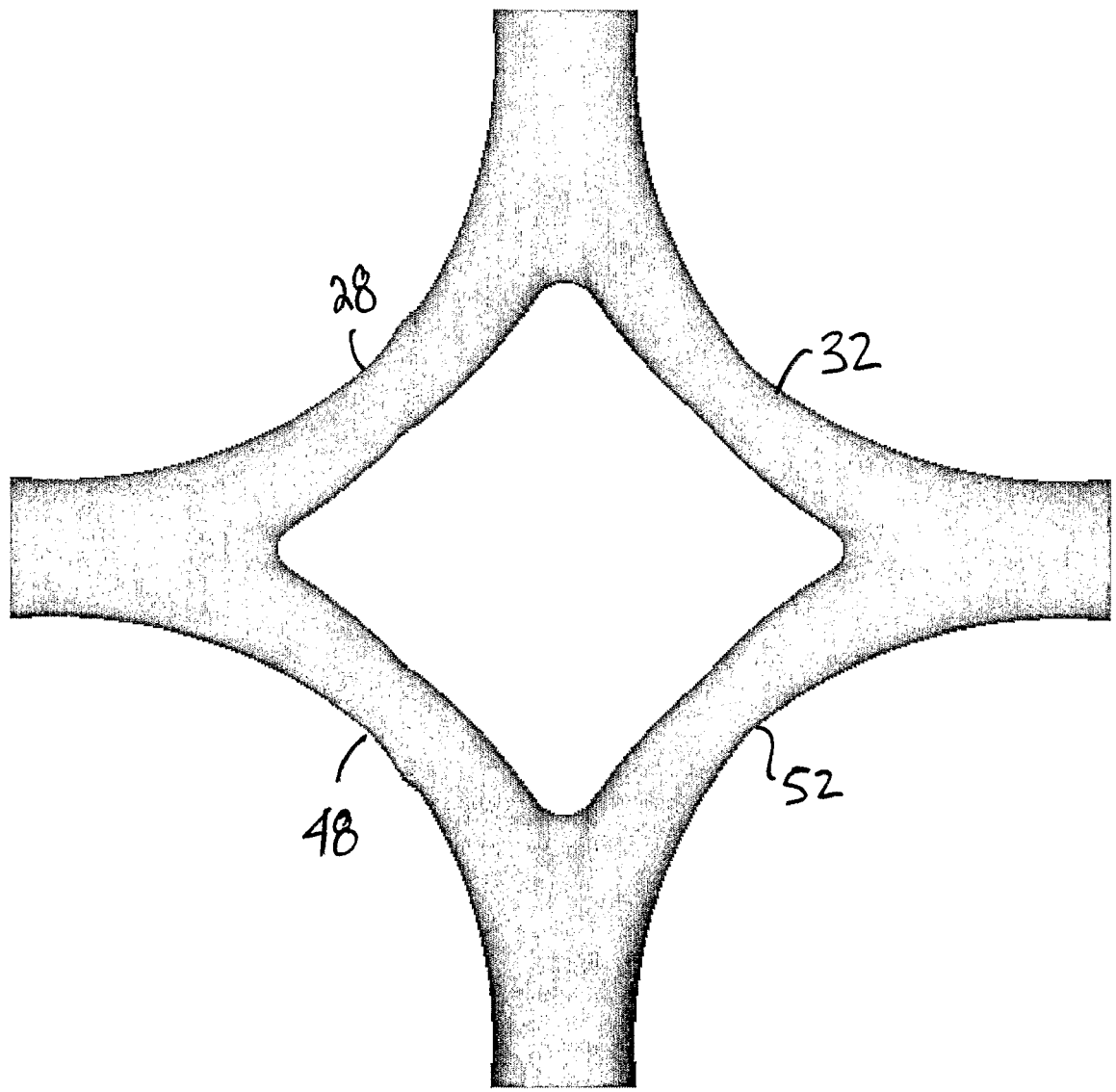
FIG. 10 is another preferred embodiment of the present invention.

Indeed, FIG. 10 illustrates the present invention 100 with path diameters non-constant along the length of the paths 28, 32, 48, 52. Changing path diameters changes the flow and pressure distribution. By increasing some path diameters and decreasing other path diameters, the blood can be more or less redirected where it is needed most.

Figure 9:
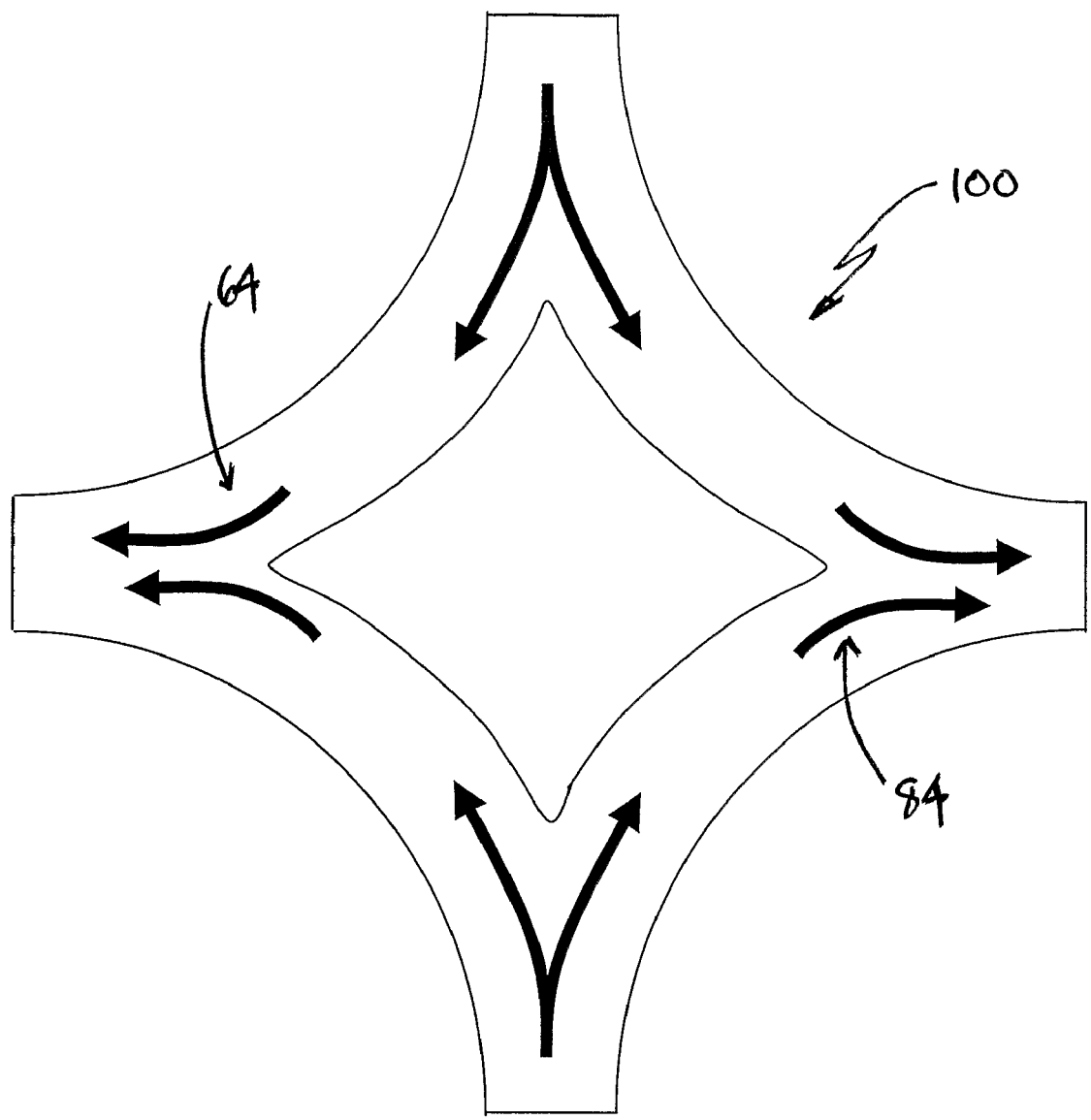
FIG. 9 is a flow diagram of the embodiment of the present invention according to FIG. 8.
Figure 13:
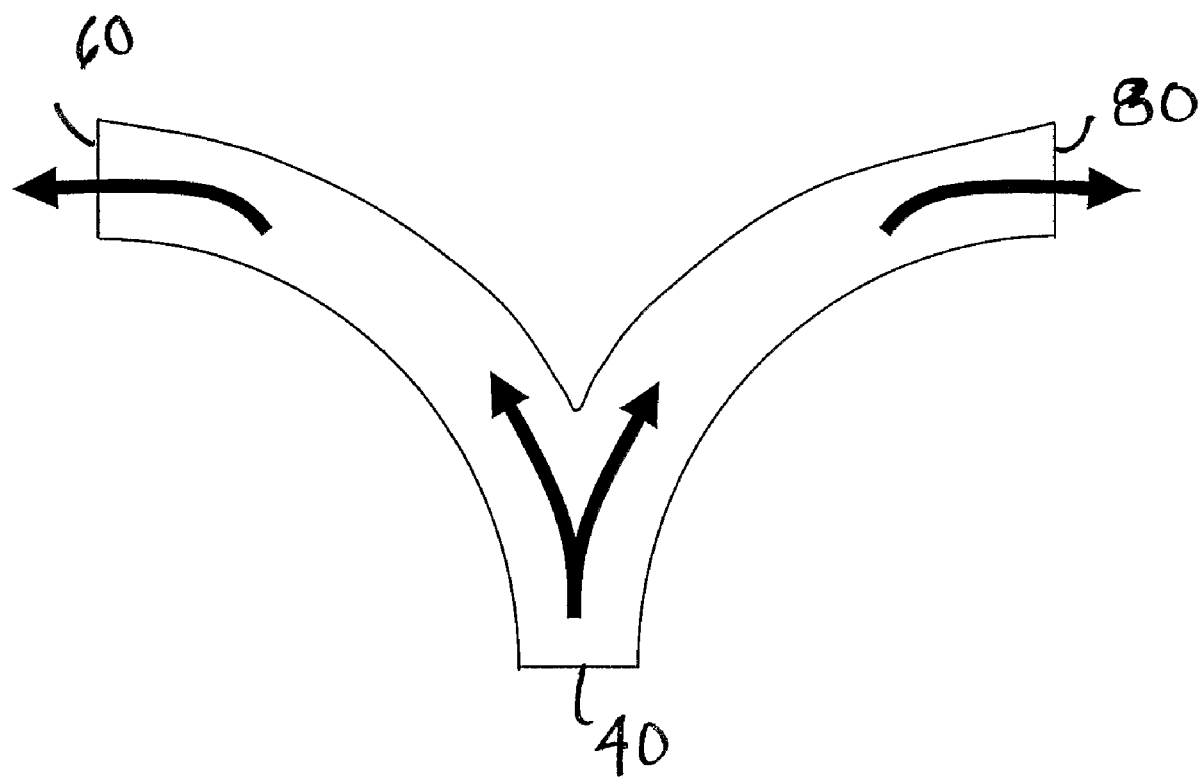
FIG. 13 is a flow diagram of a one inlet, two outlet embodiment of the present invention.
Figure 15:
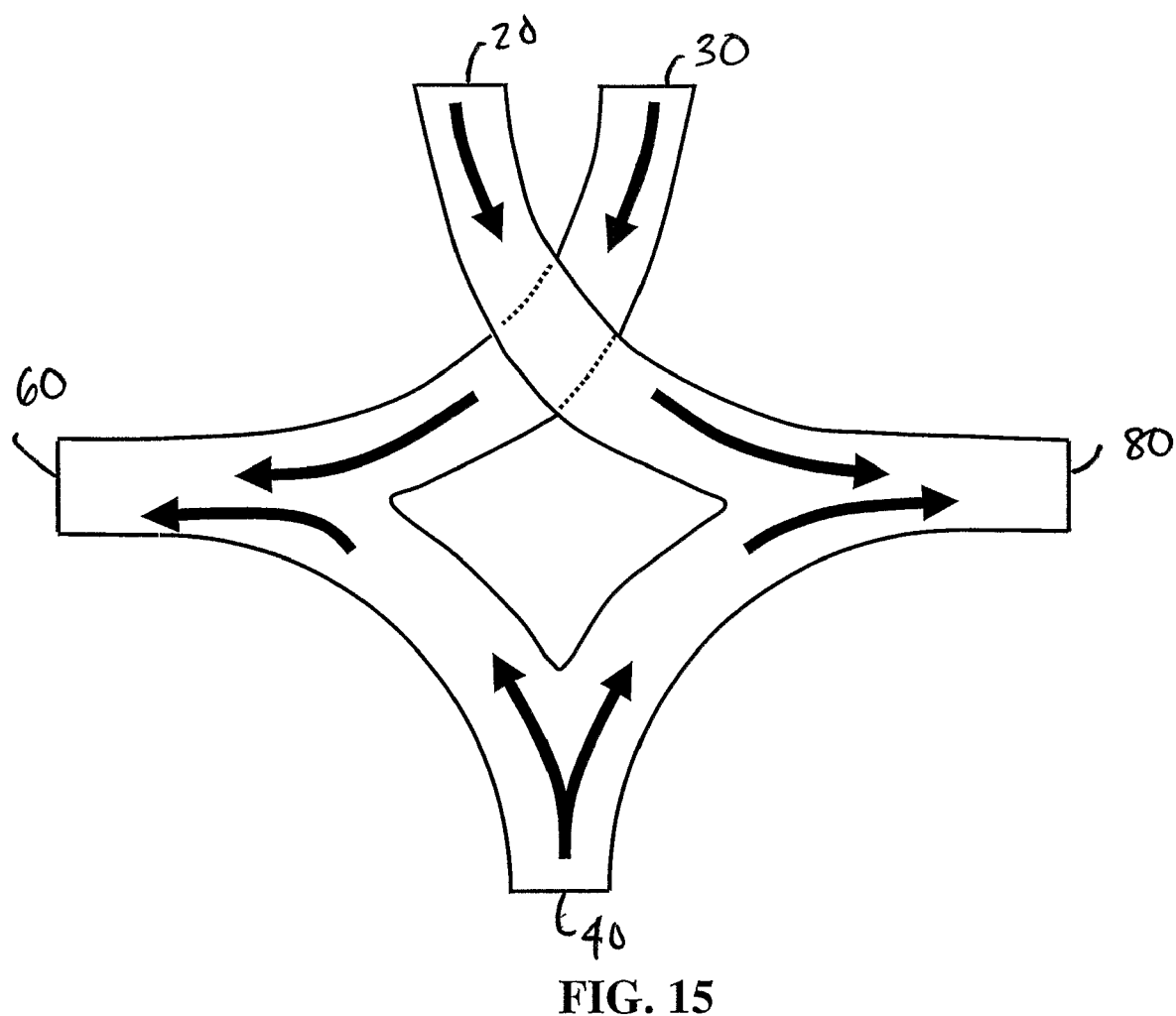
FIG. 15 is another embodiment of the device of FIG. 14.

FIG. 9 illustrates an example of flow path through a preferred embodiment of the present invention 100. As can be seen, at regions 64, 84 of merging flows, the split inlet flows mix with vectors of approximately same bearing, thus limiting momentum loss and mixing. The arrows indicating flow lines in FIGS. 9, 13 and 15 are provided merely as examples, and it will be understood that the actual flow may differ both in direction, and in shown contour.

Figure 11:
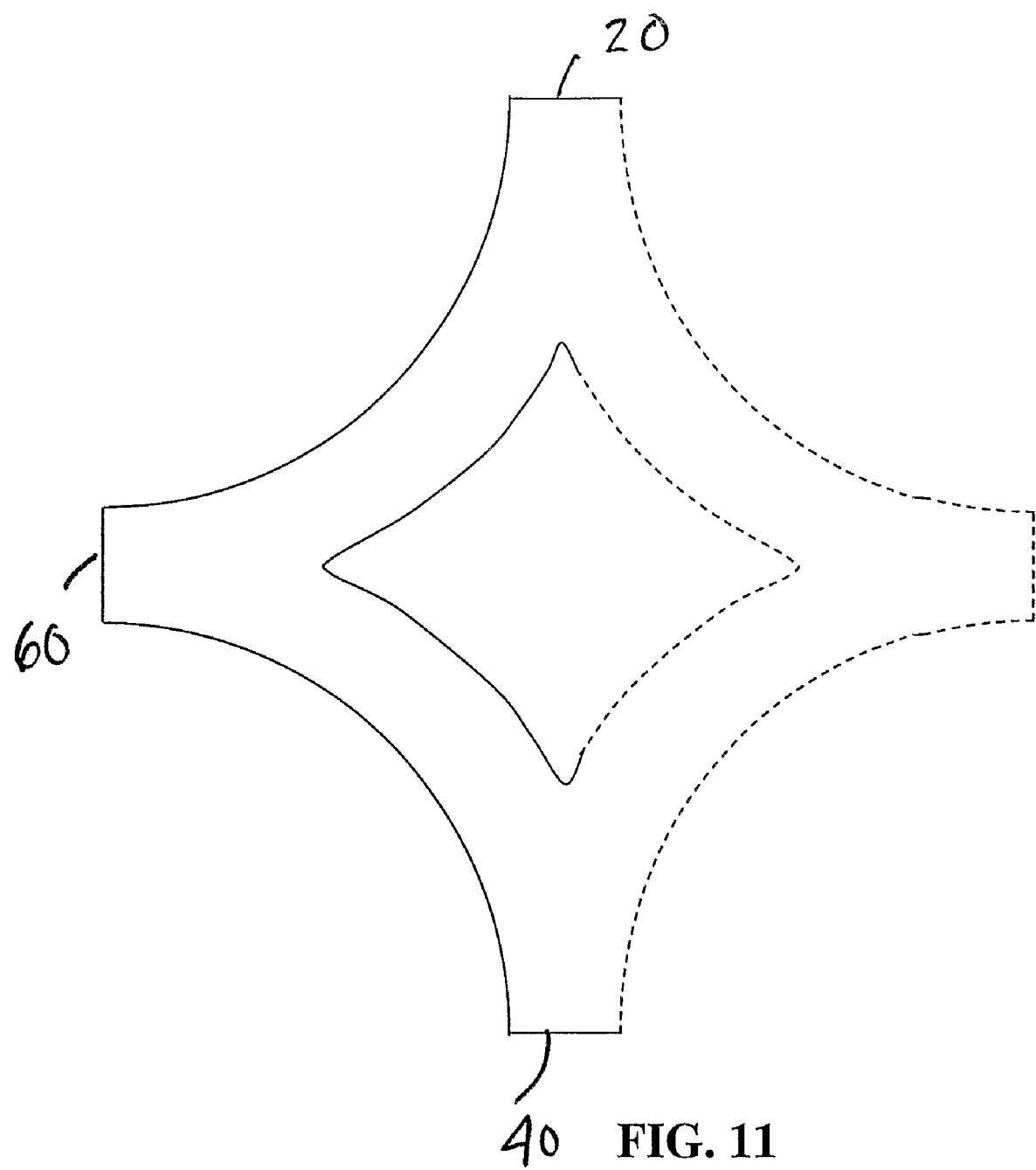
FIGS. 11-12 illustrate other embodiments of the present invention that have less than either two inlets or two outlets.
Figure 12:
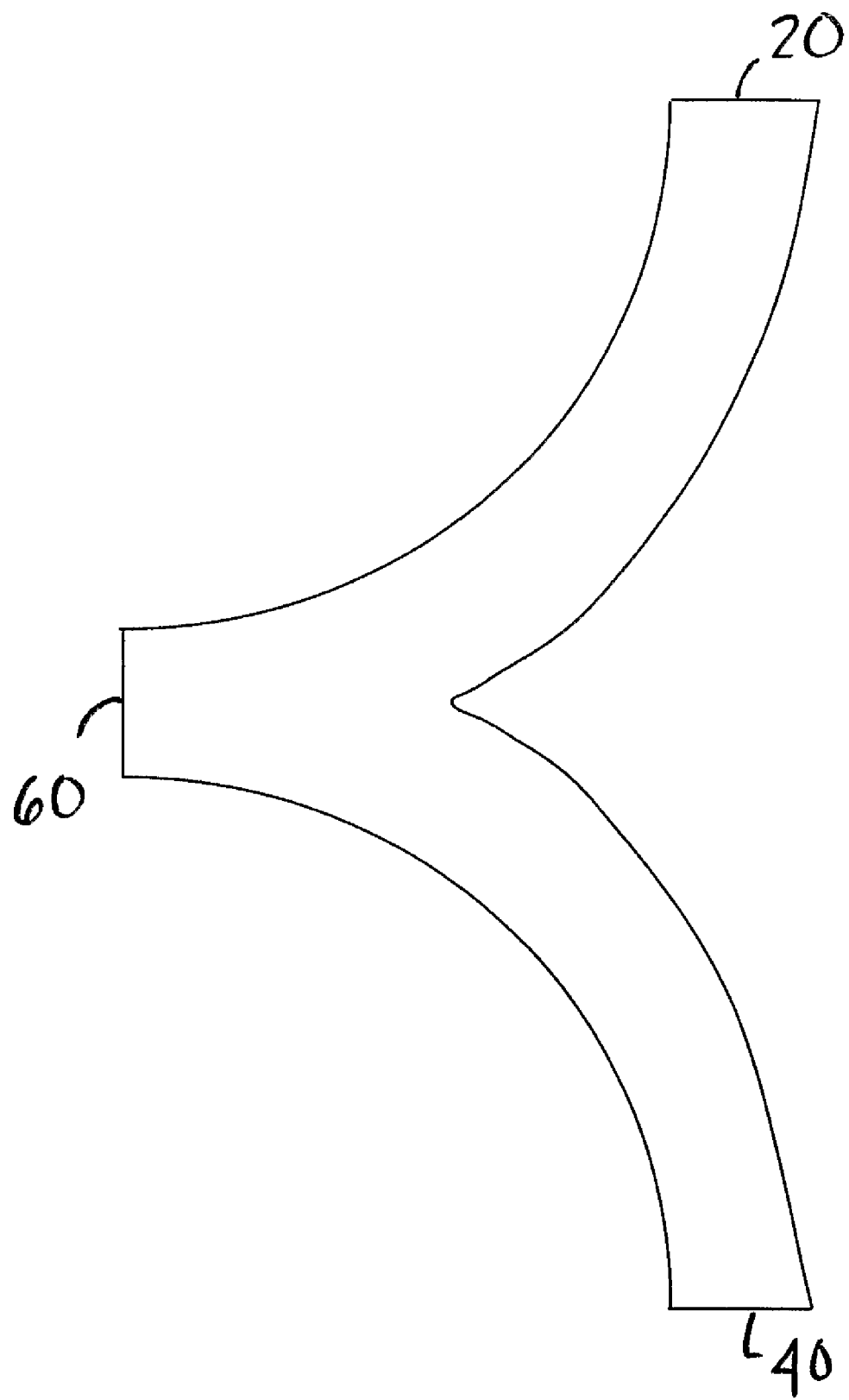

FIGS. 11 and 12 show other embodiments of the present invention 100, the device having two inlets 20, 40, and one outlet 60. FIG. 13 illustrates an example of flow path through a preferred embodiment of the present invention 100 having one inlet 40, and two outlets 60, 80. The embodiment of FIG. 13 is a 90 degree connection, unlike the Y-connection, and incorporates curvature for a smooth transition in the outlet direction. This embodiment can be used in the first stage Fontan surgery when connecting the SVC alone on the PAs.

Figure 14:
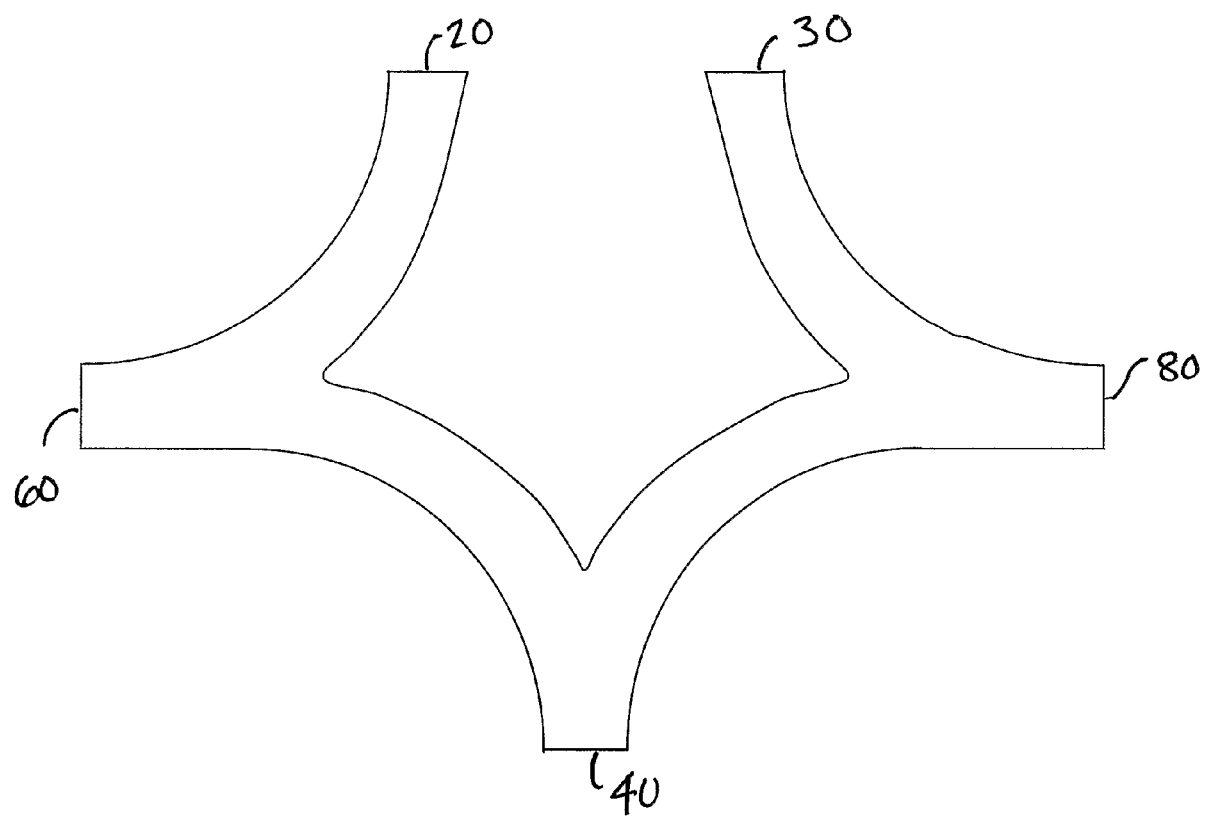
FIG. 14 is another preferred embodiment of the present invention being a bilateral SVC connection.

FIG. 14 is another embodiment of the invention, for example for a bilateral SVC, wherein the device 100 comprises three inlets, 20, 30 and 40. FIG. 15 is a variation on this design, having a cross-over bilateral SVC, providing a higher radius of curvature for the SVCs.

As seen in FIGS. 8-20, the present invention 100 preferably comprises numerous beneficial geometries, including offset between the paths/vessels, paths/vessels that curve, and those that are not necessarily in the same plane, and paths/vessels entering and exiting with different diameters.

Figure 3:
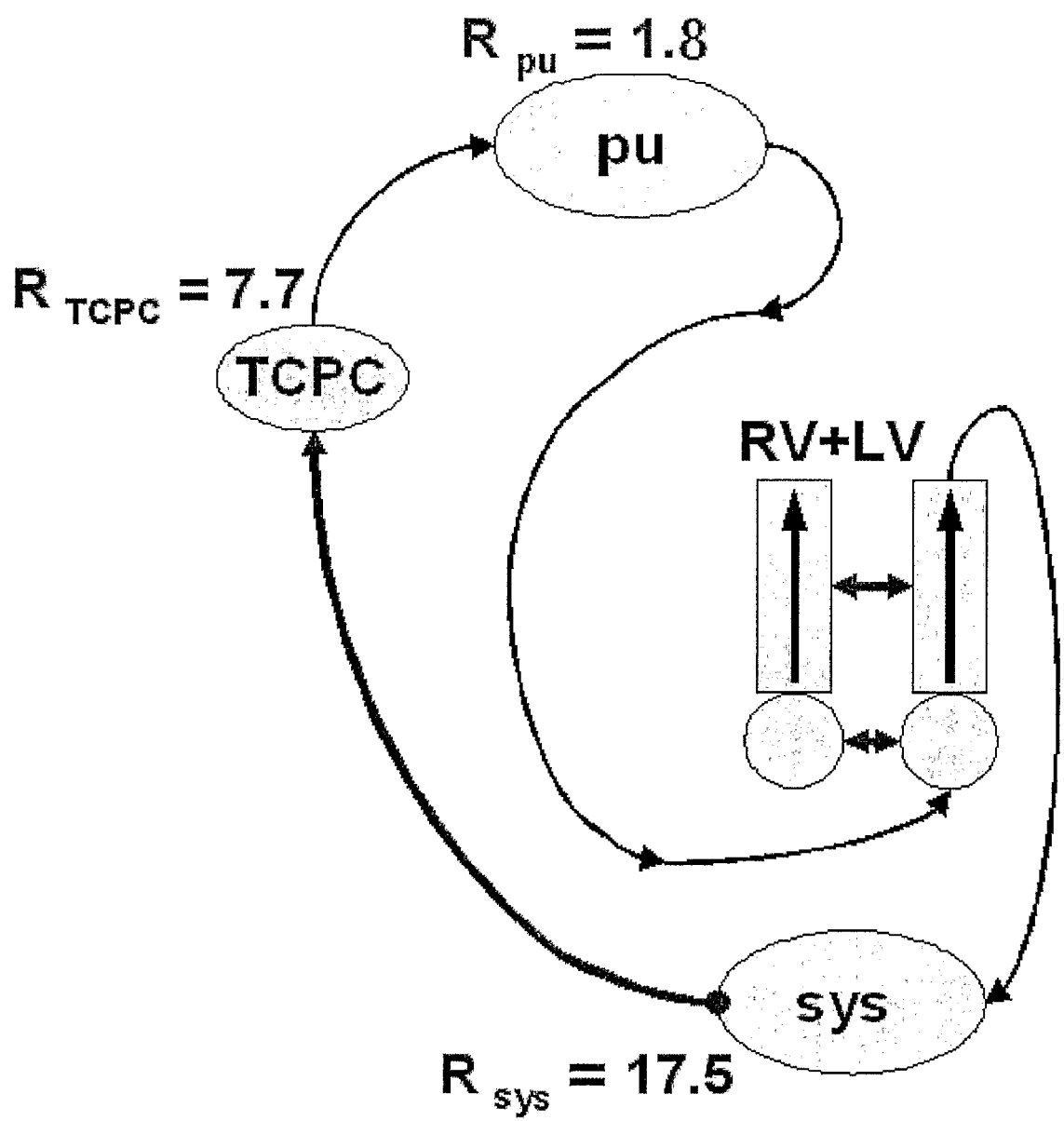
FIG. 3 illustrates single ventricle circulation after final stage Fontan surgery.
Figure 4:
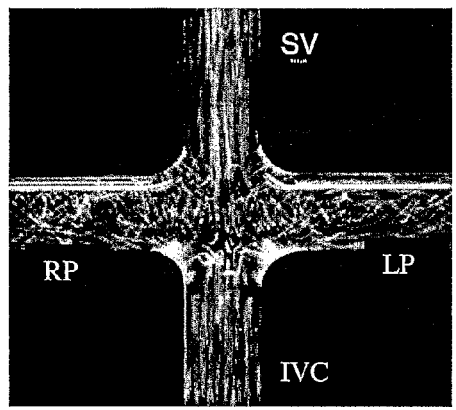
FIGS. 4 and 5 show models of prior art TCPCs with a transparent blood analog containing particles flowing through the connection to illustrate mixing and disturbance.
Figure 5:
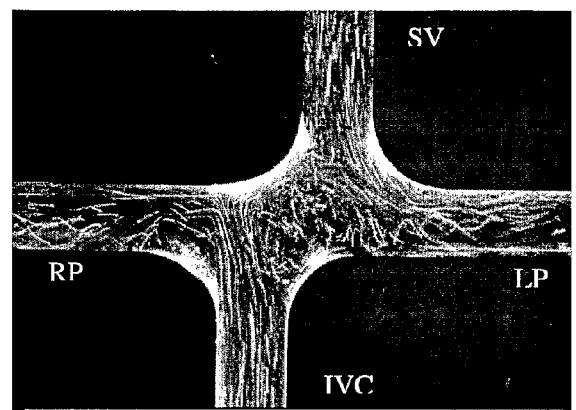
Figure 6:
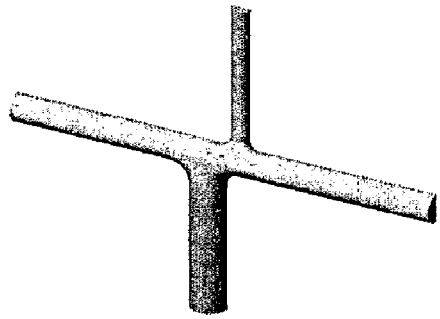
FIG. 6 illustrates a one diameter offset planar prior art TCPC model.
Figures 7A, 7B:
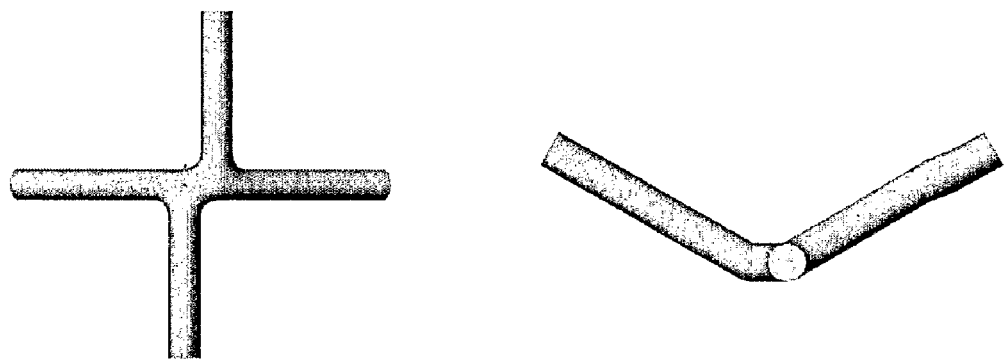
FIG. 7(a) shows a front view, and FIG. 7(b) a top view of the same connection.

Recent studies on present anatomical TCPC models indicate that the blood flow resistance through the TCPC can be quite significant for the configurations studied, comparable to the other major resistance sources of the body (like pulmonary and vascular resistances). The TCPC flow resistance depends on the connection geometry like vessel sizes, diameters, connection shape, flare, offset and stenosis. In FIG. 3, the resistance value for an intra-atrial Fontan anatomy is given which is only 56% lower than the systemic vascular resistance and 76% higher than the pulmonary vascular resistance. This resistance value for the TCPC connection is calculated from the measured pressure and flow rates of in vitro tests. Any reduction of TCPC resistance or equivalently hemodynamic power loss will enable higher flow rates, and reduce the work done by the single ventricle, and ultimately improve the quality of life. Even a couple of percentage point improvements in hydrodynamic efficiency will lead to major impact as the heart operates continuously through life.

TCPC flows have been computationally and experimentally studied through simplified models that incorporate increasingly complex anatomic features such as SVC/IVC flare, caval offset, pulmonary artery curvature and physiologic diameters. Models are valuable as they enable an essential understanding of the underlying fluid dynamics and facilitate isolation of specific hemodynamic phenomena that are integrated into complex 3D anatomic connection flow fields.

Previous studies on a one diameter IVC/SVC caval offset reference TCPC model demonstrated its low hydrodynamic energy loss characteristics due to the stable buffer vortex located at the offset region. In this model, all vena cava and pulmonary artery branches have a constant diameter of 13.335 mm, a dimension based on the chest MRI of an eight-year-old Fontan patient. The offset is defined as the distance between the caval axes. Larger offsets distances are surgically impractical to construct, but provide lower loss indices and can result in undesirable hepatic blood mixing or rather lack thereof since the blood in the offset region is rather stagnant.

Figure 21:
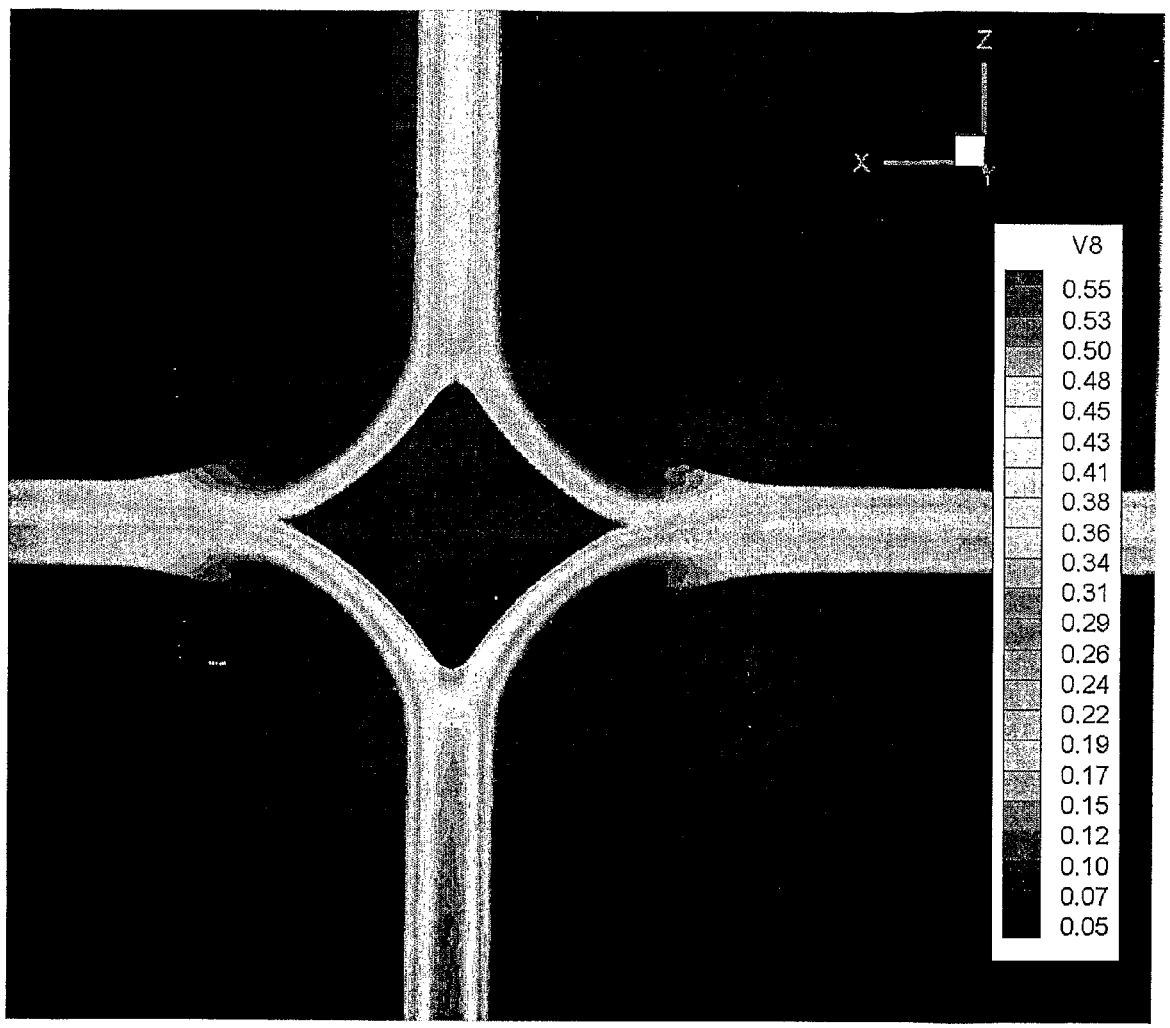
FIG. 21 illustrates computational fluid dynamics (CFD) calculations in mid-plane section of a preferred embodiment of the present invention showing in-plane velocity magnitudes.
Figure 22:
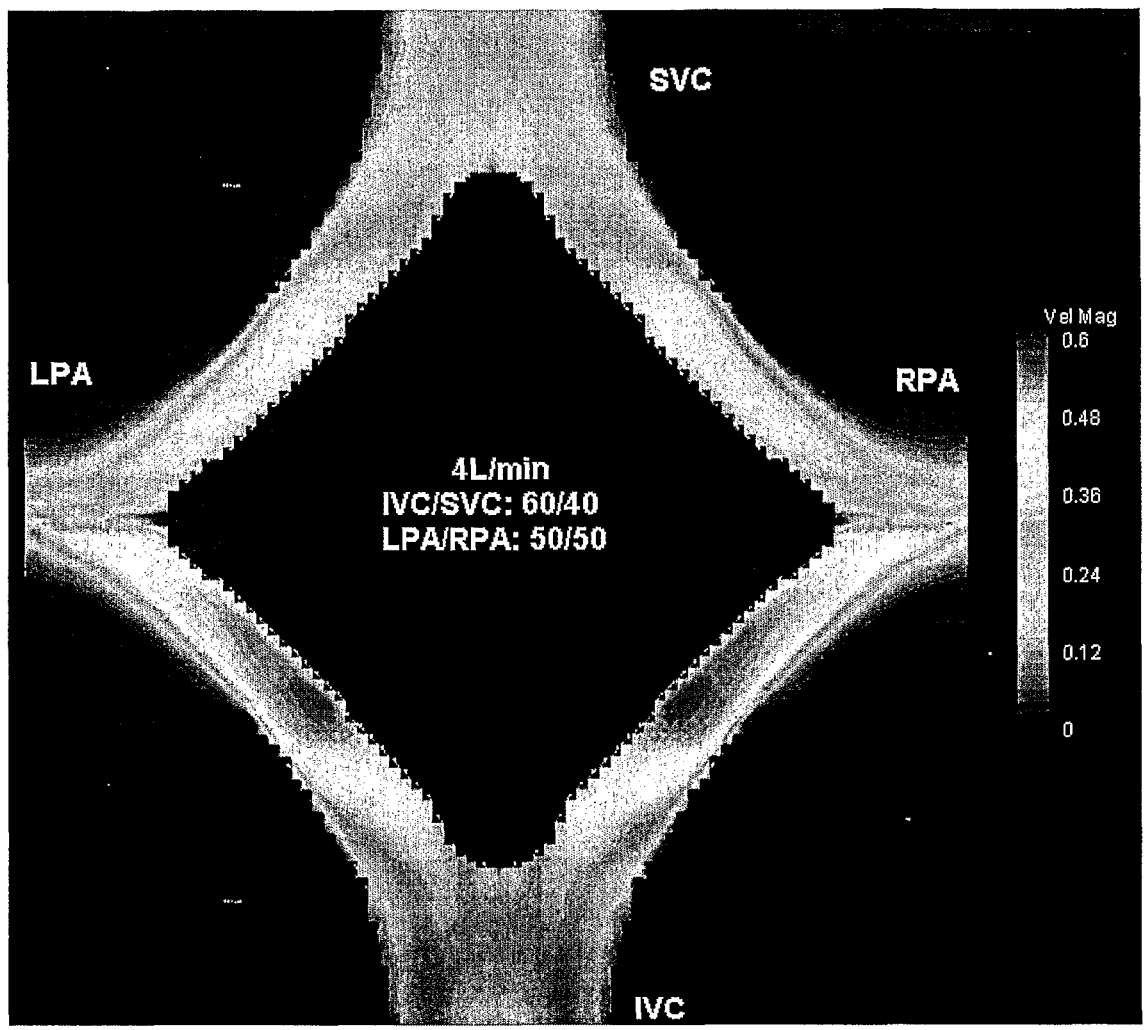
FIG. 22 is an experimental result acquired from particle image velocimetry (PIV) measurements in the mid-plane of another preferred embodiment of the present invention showing velocity magnitudes of the flow.

FIG. 21 is a CFD mid-plane of the device 100 of FIG. 8, showing in-plane velocity magnitudes shaded according to the scale on the light. FIG. 22 is a PIV mid-plane of the device 100 of FIG. 10, showing in-plane velocity magnitudes shaded according to the scale on the right.

Figure 23:
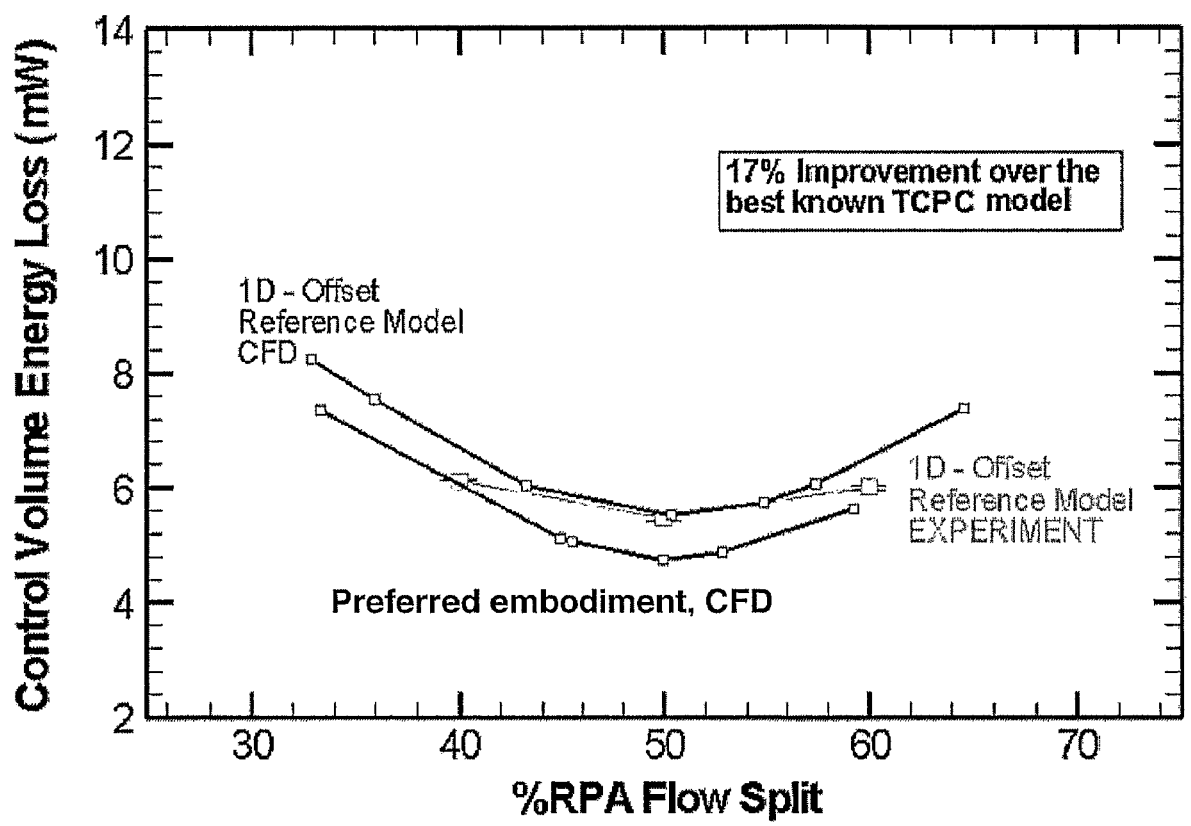
FIG. 23 is a graph of the hydrodynamic power loss comparisons of a preferred embodiment of the present invention against a one diameter offset reference model.

FIG. 23 illustrates the hydrodynamic power loss comparisons of the present invention and one diameter offset reference model at 4 L/min cardiac output, where 40% comes in via the SVC and 60% via the IVC. The present invention is compared with this one diameter offset reference model. FIG. 23 shows the power loss plots of both configurations for different flow splits. For 50/50 PA flow split, one embodiment of the present invention gives 17% lower power loss values compared to the reference conventional TCPC at 4 L/min. Improvements at higher cardiac outputs are higher, as discussed below.

Figure 24:
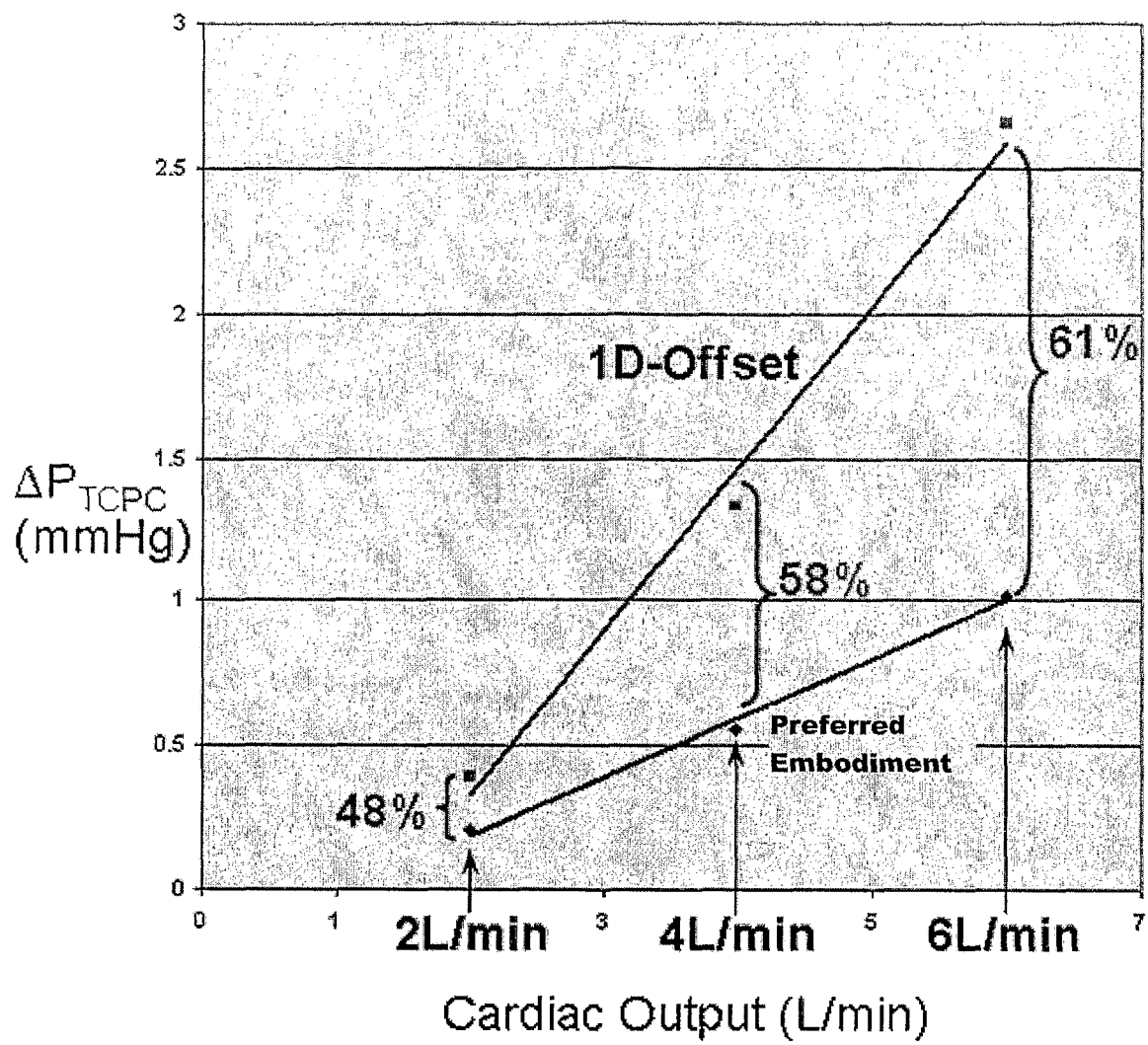
FIG. 24 is a graph of pressure drop comparisons of a preferred embodiment of the present invention against a one diameter offset reference model at different cardiac outputs.

FIG. 24 illustrates pressure drop comparisons of the present invention and a one diameter offset reference model at different cardiac outputs. During exercise conditions the effect of high flow resistance or power loss is more apparent if pressure drop (combined static and dynamic) vs. cardiac output is plotted for this suggested TCPC anatomy and the one diameter offset reference model. Slopes of the curves in FIG. 24 give the equivalent flow resistance in the corresponding TCPC. At high cardiac outputs, pressure drops are considerable consuming the pressure head supplied by the heart. Low exercise capability of Fontan patients are already highlighted in several clinical publications. Embodiments of the present invention have 48%, 58%, and 61% lower pressure drops at 2, 4 and 6 L/min cardiac outputs respectively.

Figure 25:
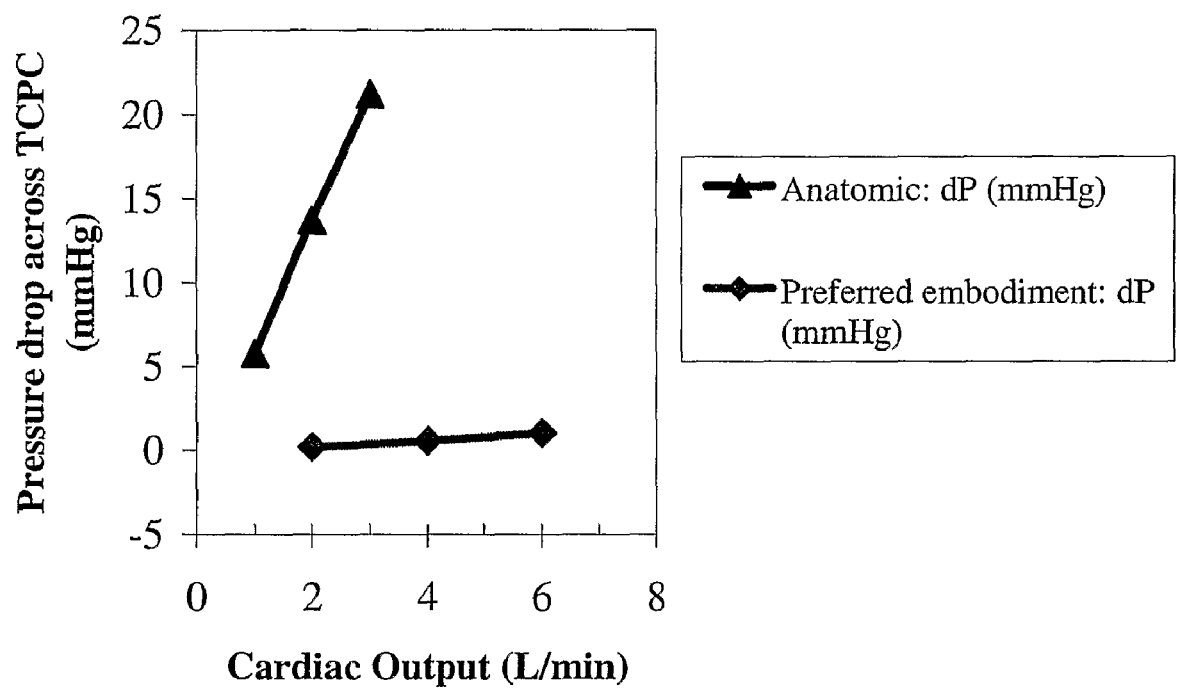
FIG. 25 is a graph comparing pressure drops (dP) between a patient-specific reconstruction of a prior art device as against the use of a preferred embodiment of the present invention.

FIG. 25 shows dP difference between a patient with a non-optimal connection, and a preferred embodiment of the present invention. The dP's were found through computational fluid dynamic calculation. Since the slope of the present invention is much smaller than the anatomic, the pressure drops over the anatomic is much higher.

The present invention also offers a controlled way of distributing the total cardiac output to both lungs. As the right lung is greater in size, more blood naturally flows to it. Such a fine distribution is not possible with the current surgical techniques, but a prefabricated graft configuration of the present invention can facilitate any split based on the patient's specific needs.

The present invention 100 is thus an approach to the Fontan connection in an effort to improve flow optimization and distribution. Experiments are showing that power loss and pressure drops across the connections between the present design and the vascular connections used in the Fontan operation could be significantly reduced, resulting in improved quality of life.

The present invention can be formed of many materials, including biocompatible materials, although preferably, the device 100 is built by tissue-engineered material that can grow with the patient. Materials can include, for example, homograft, autograft, allograft, plastics and biocompatible materials such as TEFLON, DACRON, and polytetetrafluoroethylene (PTFE).

FIG. 8 illustrates an embodiment of the present invention 100, being a most optimal configuration; however, this configuration can not be used in all cases. The final stage or Norwood III (Fontan) operation is performed early in the patient's life; usually between 18-24 months of age. Patient growth naturally results in a size mismatch between the present connection and the vascular system.

Figure 16:
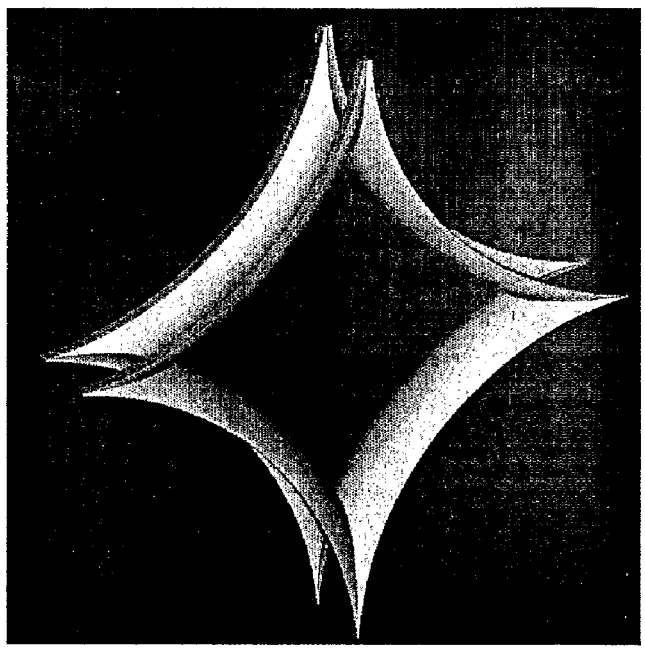
FIGS. 16-20 are other preferred embodiments of the present invention as a center piece device.

Therefore, the present invention should be formed of material that would allow adaptation to patient size, but still allow for the power loss optimized streamlined flow, and ensure as close to equal distribution as possible of the nutrient-filled hepatic blood flow to both lungs, which has been shown to be very important in lung development. The connections of FIGS. 16-17 illustrate an embodiment of the invention 100 to address this issue. This allows for partially utilizing graft material and native blood vessels. The graft material will not grow; however, the native blood vessels completing the connection are allowed to grow outwards.

In cases where the SVC is too small for division and attachment to the center-piece just described and shown in FIGS. 16-17, a variant of the present invention, a center-piece connection 200 was created, which allowed for splitting of the IVC and SVC flow. The SVC split is smaller, enabling direct attachment to the graft without creating stenotic areas at the SVC attachment site (FIGS. 18-20).

It is apparent that the various preferred embodiments of the present invention provide numerous advantages over the current TCPC designs allowing for the combination of IVC/SVC flows at angles greater than zero. For example, the embodiment of the present invention as shown in FIG. 8 is advantageous, for, among other reasons:

Nutrient filled hepatic blood equally distributed to both lungs.

Streamlined flow reduces power losses significantly, which reduces the workload on the univentricular heart.

No stagnant flow, which otherwise could cause thrombus formation.

Negative pulmonary pressure during inspiration causes more efficient flow towards lungs than in other Fontan connections. This increases the flow, which in turn increases the cardiac output. Reduced cardiac output is the major mortality cause.

Suture lines kept at a minimum (only necessary to suture at inlets and outlets).

Fast and easy to deploy.

More adaptive to flow split changes than other configurations.

The embodiment of the present invention as shown in FIGS. 16-17 also has numerous advantages, including:

Nutrient filled hepatic blood equally distributed to both lungs.

Streamlined flow reduces power losses significantly, which reduces the workload on the univentricular heart.

No stagnant flow, which otherwise would cause thrombus formation.

Negative pulmonary pressure during inspiration causes more efficient flow towards lungs than in other Fontan connections. This increases the flow, which in turn increases the cardiac output. Reduced cardiac output is the major mortality cause.

More adaptive to flow split changes than other configurations.

Connection and vessel diameters will grow with patient growth.

The embodiment of the present invention as shown in FIGS. 18-20 has its own advantages, including:

Nutrient filled hepatic blood equally distributed to both lungs.

Streamlined flow reduces power losses significantly, which reduces the workload on the univentricular heart.

No stagnant flow, which otherwise would cause thrombus formation.

Negative pulmonary pressure during inspiration causes more efficient flow towards lungs than in other Fontan connections. This increases the flow, which in turn increases the cardiac output. Reduced cardiac output is the major mortality cause.

More adaptive to flow split changes than other configurations.

Connection and vessel diameters will grow with patient growth.

In cases where SVC diameter is too small to split, this can be used instead of the graft shown in FIGS. 16-17.

While the invention has been disclosed in its preferred forms, it will be apparent to those skilled in the art that many modifications, additions, and deletions can be made therein without departing from the spirit and scope of the invention and its equivalents as set forth in the following claims.

What is claimed is:

1. A method for limiting flow disturbance in an energy efficient manner comprising:
   providing a flow merging device;
   splitting a first inlet flow at the flow merging device into a first branch and a second branch;
   splitting a second inlet flow at the flow merging device into a first branch and a second branch; and
   merging the first branches of the first and second inlet flows together; wherein the flows in each of the first branches are substantially parallel at the site of merging.

2. The method according to claim 1, further comprising merging the second branches of the first and second inlet flows together, wherein the flows in each of the second branches are substantially parallel at the site of merging.

3. The method according to claim 2, wherein the flow rates in the merged first branches and the merged second branches are substantially equal.

4. The method according to claim 1, wherein the first inlet flow is a flow of blood.

5. The method according to claim 4, further comprising directing the flow of the merged first branches to a lung.

6. The method according to claim 4, further comprising directing the flow of the merged second branches to a lung.

7. The method according to claim 1, wherein the flow merging device comprises tissue-engineered material.

8. A device for merging at least two inlet flows, and thereafter directing portions of each inlet flow to at least two outlets in an energy efficient manner, the device comprising:
   a first connection inlet to receive a first liquid flow and guide the first liquid flow toward a first outlet and a second outlet;
   a second connection inlet to receive a second liquid flow and guide the second liquid flow toward the first outlet and the second outlet;
   a first outlet chamber, in liquid communication with the first outlet, sized and shape to receive a portion of the first liquid flow and a portion of the second liquid flow and merge the flows in a substantially parallel fashion for provision to the first outlet; and
   a second outlet chamber, in liquid communication with the second outlet, sized and shape to receive a portion of the first liquid flow and a portion of the second liquid flow and merge the flows in a substantially parallel fashion for provision to the second outlet.

9. The device of claim 8, wherein the first and second outlets are sized and shaped to have substantially equal flow rates therethrough.

10. The device of claim 8, wherein the device is for use where at least one of the inlet flows is a flow of blood.

11. The device of claim 10, wherein at least one of the outlets directs flow to a lung.

12. The device of claim 8, wherein the device comprises tissue-engineered material.

13. A method for limiting venous blood flow disturbance from the systemic to the pulmonary circulation in an energy efficient manner comprising:
   providing a flow merging device;
   splitting the IVC flow at the flow merging device into a first branch and a second branch;
   splitting the SVC flow at the flow merging device into a first branch and a second branch; and
   merging the first branches of the IVC and SVC flows together;
   wherein the flows in each of the first branches are substantially parallel at the site of merging.

14. The method according to claim 13, further comprising merging the second branches of the IVC and SVC flows together, wherein the flows in each of the second branches are substantially parallel at the site of merging.

15. The method according to claim 14, wherein the flow rates in the merged first branches and the merged second branches are substantially equal.

16. The method according to claim 14, further comprising directing the flow of the merged first branches to a lung.

17. The method according to claim 14, further comprising directing the flow of the merged second branches to a lung.

18. The method according to claim 13, wherein the flow merging device comprises tissue-engineered material.

19. A method of performing a surgical procedure on the heart of a patient comprising:
   providing a flow merging device;
   splitting the IVC flow at the flow merging device into a first branch and a second branch;
   splitting the SVC flow at the flow merging device into a first branch and a second branch; and
   merging the first branches of the IVC and SVC flows together; wherein the flows in each of the first branches are substantially parallel at the site of merging.

20. The method according to claim 19, wherein the flow merging device comprises:
   an IVC inlet at which the IVC is connected to the flow merging device;
   a SVC inlet at which the SVC is connected to the flow merging device;
   a first outlet at which the first branches of the IVC and SVC flows combine; and
   a second outlet at which the second branches of the IVC and SVC flows combine.

21. A device for combining the flow of the IVC and the SVC in an energy efficient manner, and thereafter directing the combined flow to the lungs, the device comprising:
   an IVC inlet at which the IVC is connected, the IVC inlet splitting a portion of the IVC flow between a first branch and a second branch;
   a SVC inlet at which the SVC is connected, the SVC inlet splitting a portion of the SVC flow between a first branch and a second branch;
   a first pulmonary outlet at which the first branches of the IVC and SVC flows combine, the first pulmonary outlet being in liquid communication with a first outlet chamber having opposing curved features that combine the IVC and SVC flows and enable the combined IVC-SVC flows to commonly exit the first lung outlet; and
   a second pulmonary outlet at which the second branches of the IVC and SVC flows combine, the second pulmonary outlet being in liquid communication with a second outlet chamber having opposing curved features that combine the IVC and SVC flows and enable the combined IVC-SVC flows to commonly exit the second lung outlet,
   wherein the flows in each of the first branches and second branches are substantially parallel at the sites of combining the flows.

22. A method of using a device for combining the flow of the IVC and the SVC, and thereafter directing the combined flow to the lungs, the method comprising:
   providing a device, the device comprising:
      an IVC inlet at which the IVC is connected, the IVC inlet splitting a portion of the IVC flow between a first branch and a second branch;
      a SVC inlet at which the SVC is connected, the SVC inlet splitting a portion of the SVC flow between a first branch and a second branch;
      a first pulmonary outlet at which the first branches of the IVC and SVC flows combine; and
      a second pulmonary outlet at which the second branches of the IVC and SVC flows combine,
      wherein the flows in each of the first branches and second branches are substantially parallel at the sites of combining the flows;
   flowing a liquid through the device; and
   using the device ex vivo.

* * * * *

UNITED STATES PATENT AND TRADEMARK OFFICE
CERTIFICATE OF CORRECTION

| | | |
|---|---|---|
| PATENT NO. | : 7,811,244 B2 | Page 1 of 1 |
| APPLICATION NO. | : 10/593855 | |
| DATED | : October 12, 2010 | |
| INVENTOR(S) | : Dennis Dam Sorensen et al. | |

It is certified that error appears in the above-identified patent and that said Letters Patent is hereby corrected as shown below:

Title page,

Item (75), Inventors: the third inventor's name and city should read

--Kerem Pekkan, Athens, GA (US);--

Signed and Sealed this

Seventh Day of December, 2010

David J. Kappos
*Director of the United States Patent and Trademark Office*